(12) United States Patent
Wang et al.

(10) Patent No.: US 7,372,937 B2
(45) Date of Patent: May 13, 2008

(54) SYSTEMS AND METHODS OF NON-STANDARD SPIRAL CONE-BEAM COMPUTED TOMOGRAPY (CT)

(75) Inventors: Ge Wang, Iowa City, IA (US); Yangbo Ye, Coralville, IA (US)

(73) Assignee: University of Iowa Research Foundation, Kowa City, IA (US)

( * ) Notice: Subject to any disclaimer, the term of this patent is extended or adjusted under 35 U.S.C. 154(b) by 110 days.

(21) Appl. No.: 11/182,504

(22) Filed: Jul. 15, 2005

(65) Prior Publication Data
US 2006/0050842 A1 Mar. 9, 2006

Related U.S. Application Data

(60) Provisional application No. 60/588,682, filed on Jul. 16, 2004.

(51) Int. Cl.
*H05G 1/60* (2006.01)

(52) U.S. Cl. .............................. 378/16; 378/4; 378/901

(58) Field of Classification Search .................. 378/16, 378/4–20, 901
See application file for complete search history.

(56) References Cited

U.S. PATENT DOCUMENTS

| | | | |
|---|---|---|---|
| 5,463,666 A * | 10/1995 | Eberhard et al. .............. 378/4 |
| 5,473,658 A | 12/1995 | Wallschlaeger |
| 5,909,476 A | 6/1999 | Cheng et al. |
| 5,987,157 A | 11/1999 | Schaller et al. |
| 5,995,580 A | 11/1999 | Schaller |
| 6,018,561 A * | 1/2000 | Tam .............. 378/4 |
| 6,075,836 A | 6/2000 | Ning |
| 6,240,157 B1 | 5/2001 | Danielsson |
| 6,252,926 B1 | 6/2001 | Flohr et al. |
| 6,381,297 B1 | 4/2002 | Hsieh |
| 6,452,997 B1 | 9/2002 | Muller et al. |
| 6,459,756 B1 | 10/2002 | Tam et al. |
| 6,504,892 B1 * | 1/2003 | Ning ............................. 378/4 |
| 6,574,299 B1 | 6/2003 | Katsevich |
| 6,658,081 B2 | 12/2003 | Bruder et al. |
| 6,665,370 B2 | 12/2003 | Bruder et al. |
| 6,865,246 B2 * | 3/2005 | Yang ............................. 378/4 |
| 2002/0141628 A1 | 10/2002 | Bruder et al. |
| 2003/0161443 A1 | 8/2003 | Xiao et al. |
| 2003/0161444 A1 * | 8/2003 | Katsevich .................... 378/210 |

(Continued)

OTHER PUBLICATIONS

Ramamurthi et al. Exact 3D Cone-beam Reconstruction from Projections Obtained Over a Wobble Trajectory on a C-arm, Biomedical Imaging: Marco to Nano, Apr. 15-18, 2004, pp. 932-935, vol. 1.*

(Continued)

*Primary Examiner*—Courtney Thomas
*Assistant Examiner*—Alexander H Taningco
(74) *Attorney, Agent, or Firm*—Needle & Rosenberg, P.C.

(57) ABSTRACT

Provided herein are methods of reconstructing an image from projection data provided by a tomography scanner that is based on geometric optics comprising scanning an object in a cone-beam imaging geometry following a non-standard spiral path or a general piecewise smooth scanning path wherein projection data is generated and reconstructing an image according to a closed-form formula that is either in the filtered backprojection (FBP) or backprojection filtration (or backprojected filtration, BPF) formats. Also provided herein are associated systems and apparatuses for tomographic imaging.

34 Claims, 11 Drawing Sheets

U.S. PATENT DOCUMENTS

2005/0249432 A1* 11/2005 Zou et al. .................. 382/276
2006/0291611 A1* 12/2006 Pack et al. .................... 378/4
2007/0036418 A1*  2/2007 Pan et al. ................... 382/131

OTHER PUBLICATIONS

Zou et al., Theory and algorithms for image reconstruction on chords and within regions of interest, Optical Society of America, 2005, pp. 2372-2384.*
Yu et al., A Rebinning-type Backprojection-Filteration Algorithm for Image Reconstruction in Helical Cone-beam CT, IEEE Nuclear Science Symposium Conference Record, 2006, pp. 2869-2872.*
NIH/NIBIB Grant 1R21EB004287-01, Apr. 17, 2005 (EB004287), "Bolus Chasing CT Angiography Using Adaptive Control."
NIH/NIBIB Grant 1R01EB002667-01, Sep. 30, 2003-Jul. 31, 2008 (EB002667), "Cone-Beam Methods for Dynamic Volumetric X-Ray CT."
Barger AV, W.F. Block, Y Toropov, TM Grist, and CA Mistretta, "Time-resolved contrast-enhanced imaging with isotropic resolution and broad coverage using an undersampled 3D projection trajectory," 2002, Magn. Reson. Med., 48:297-305.
Bollano E, F Waagstein, et al. "Stress echocardiography using transesophageal atrial pacing in rats," 2003, J. Am. Soc. Echocardiogr, 16(4):326-332.
Boyd DP and MJ Lipton, "Cardiac computed tomography," 1983, Proc. IEEE, 71:298-307.
Chien KR, "Meeting Koch's postulates for calcium signaling in cardiac hypertrophy," 2000, J Clin Invest, 105(10):1339-1342.
Collins KA, CE Korcarz, et al., "Use of echocardiography for the phenotypic assessment of genetically altered mice," 2003, Physiol. Genomics, 13(3):227-239.
Defrise M, F Noo et al., "A solution to the long-object problem in helical cone-beam tomography," 2000, Phys Med Biol, 45:623-643.
Defrise M, Townsend DW, Clark R, "Three-dimensional image reconstruction from complete projections," 1989, Phys Med Biol, 34:573-587.
Feldkamp LA, LC Davis, and JW Kress, "Practical cone-beam algorithm," 1984, J. Opt. Soc. Am., 1(A):612-619.
Feldman MD, JM Erikson, et al., "Validation of a mouse conductance system to determine LV volume: comparison to echocardiography and crystals," 2000, Am. J. Physiol. Heart. Circ. Physiol., 279(4):H1698-H1707.
Ge S, JG Warner Jr, TP Abraham, ND Kon, RF Brooker, AM Nomeir, KM Fowle, P Burgess, and DW Kitzman, "Three-dimensional surface area of the aortic valve orifice by three-dimensional echocardiography: Clinical validation of a novel index for assessment of aortic stenosis," 1998, Amer. Heart J.,. 136(6):1042-1050.
Ge S, M Jones, T Shiota, I Yamada, CG DeGroff, DE Teien, AM Baptisa, and DJ Sahn, "Quantitation of Mitral Flow by Doppler Color Flow Mapping," 1996, J. Amer. Soc. Echocardiography, 9(5):700-709.
Ikeda Y and J Ross Jr., "Models of dilated cardiomyopathy in the mouse and the hamster," 2000, Curr Opin Cardiol, 15(3):197-201.
James JF, TE Hewett, et al., "Cardiac physiology in transgenic mice," 1998, Circ. Res., 82(4):407-415.
Katsevich A, "Improved exact FBP algorithm for spiral CT," 2004, Adv Appl Math, 32:681-697.
Katsevich A, "A general scheme for constructing inversion algorithms for cone beam CT," 2003, Int'l J of Math and Math, Sci. 21:1305-1321.
Katsevich A, "Theoretically exact filtered backprojection-type inversion algorithm for spiral CT," 2002, SIAM Journal on Applied Mathematics, 62:2012-2026.
Molkentin JD, "Calcineurin and beyond: cardiac hypertrophic signaling," 2000 Circ. Res. 87(9):731-738.
Mor-Avi V, C Korcarz, et al., "Quantitative evaluation of left ventricular function in a Transgenic Mouse model of dilated cardiomyopathy with 2-dimensional contrast echocardiography," 1999, J. Am. Soc. Echocardiogr., 12(3):209-214.

Nahrendorf M, F Wiesmann, et al., "Serial cine-magnetic resonance imaging of left ventricular remodeling after myocardial infarction in rats," 2001, J. Magn. Reson. Imaging 14(5):547-555.
Nahrendorf M, KH Hiller, et al., "Cardiac magnetic resonance imaging in small animal models of human heart failure," Med. Image Anal. 7(3):369-375.
Nemoto S, G DeFreitas, et al., "Effects of changes in left ventricular contractility on indexes of contractility in mice," 2002, Am. J. Physiol. Heart Circ. Physiol., 283(6): H2504-H2510.
Noo F, M Defrise, R Clackdoyle, and H Kudo, "Image reconstruction from fan-beam projections on less than a short scan," 2002, Phys. Med. Biol., 47:2525-2546.
Noo F, et al., "Exact helical reconstruction using native cone-beam geometries," 2003, Physics in Medicine and Biology, 48:3787-3818.
Orlov SS, "Theory of three dimensional reconstruction. I. Conditions for a complete set of projections," 1975, Sov. Phys. Crystallogr., vol. 20:312-314.
Orlov SS, "Theory of three dimensional reconstruction. II. The recovery operator," 1975, Sov. Phys. Crystallogr., vol. 20:429-433.
Pack JD, et al., "Cone-beam reconstruction using the backprojection of locally filtered Projections," 2005, IEEE Trans. Med. Imaging, 24:70-85.
Pack JD, Noo F, Kudo H, "Investigation of saddle trajectories for cardiac CT imaging in cone-beam geometry," 2004, Phys Med Biol, 49-2317-2336.
Patten RD, MJ Aronovitz, et al., "Use of pulse wave and color flow Doppler echocardiography in mouse models of human disease," 2002, J. Am. Soc. Echocardiogr., 15(7):708-714.
Proksa R, Th Koehler, M Grass, and J Timmer, "The n-Pl-method for helical cone-beam CT," 2000, IEEE Trans. Med. Imaging 19:848-863.
Qu P, M Hamada, et al., "Time-course changes in left ventricular geometry and function during the development of hypertension in Dahl salt-sensitive rats," 2000, Hypertens. Res., 23(6):613-623.
Rehwald WG, SB Reeder, et al., "Techniques for high-speed cardiac magnetic resonance imaging in rats and rabbits," 1997, Magn. Reson. Med., 37(1):124-130.
Roberts R, AJ Marian, and L Bachinski, "Molecular genetics of hypertrophic cardiomyopathy," 1996, J. Card. Fail., 2(4 Suppl):S87-S95.
Schwarz ER, C Pollick, et al., "A small animal model of non-ischemic cardiomyopathy and its evaluation by transthoracic echocardiography," 1998, Cardiovas. Res., 39(1):216-223.
Schwarz ER, C Pollick, et al., "Evaluation of cardiac structures and function in small experimental animals: transthoracic, transesophageal, and intraventricular echocardiography to assess contractile funtion in rat heart," 1998, Basic Res. Cardiol., 93(6):477-486.
Shah G and R Roberts, "Molecular genetics of cardiomyopathies," 2000, J. Nucl Cardiol, 7(2):159-170.
Stypmann J, K Glaser, et al., "Dilated cardiomyopathy in mice deficient for the lysosomal cysteine peptidase cathepsin L," 2002, Proc. Natl. Acad. Sci. USA, 99(9):6234-6239.
Tam KC, S Samarasekera, and F Sauer, "Exact cone-beam CT with a spiral scan," 1998, Phys Med Biol, 43:1015-1024.
Towbin JA, "Molecular genetic aspects of cardiomyopathy," 1993, Biochem. Med. Metab. Biol. 49(3):285-320.
Tuy HK, "An inversion formula for cone-beam reconstruction," 1983, SIAM J Appl Math, 43:546-552.
Wang G, et al., "Top-level design and preliminary physical analysis for the first electron-beam micro-CT scanner," 2004, Journal of X-ray Sci and Tech, 12:251-260.
Wang L, C Fan, SE Topol. EJ Topol, and Q Wang, "Mutation of MEF2A in an inherited disorder with features of coronary artery disease," 2003, Science, 302(5650):1578-1581.
Wang G, SY Zhao, and D Heuscher, "A knowledge-based cone-beam x-ray CT algorithm for dynamic volumetric cardiac imaging," 2002, Med. Phys., 29:1807-1822.
Wang Y, "Signal transduction in cardiac hypertrophy—dissecting compensatory versus pathological pathways utilizing a transgenic approach," 2001, Curr Opin Pharmacol, 1(2):134-140.

Wang G, CR Crawford, and WA Kalender, "Multirow detector and cone-beam spiral/helical CT," 2000, *IEEE Trans. Med. Imaging*, 19:817-821.

Wang G, TH Lin, et al., "Half-scan cone-beam x-ray microtomography formula," 1994, *Scanning* 16(4):216-220.

Wang G, TH Lin, PC Cheng, and DM Shinozaki, "A general cone-beam reconstruction algorithm," 1993, *IEEE Trans. Med. Imaging*, 12:486-496.

Watkins H, "Genetic clues to disease pathways in hypertrophic and dilated cardiomyopathies," 2003, *Circulation*, 107(10):1344-1346.

Ye Y and Wang G, "Filtered backprojection formula for exact image reconstruction from cone-beam data along a general scanning curve," 2005, *Med. Phys.*, 32:42-48.

Ye Y, Shiying Zhao, Hengyong Yu, and Ge Wang, "Exact reconstruction for cone-beam CT along nonstandard spirals and other curves," 2004, *Proceedings of SPIE, Developments in X-Ray Tomography IV*, 5535:293-300.

Ye, Y, J Zhu and G Wang, "Minimum Detection Windows, PI-line Existence and Uniqueness for Helical Cone-Beam Scanning of Variable Pitch," 2004a, *Med. Phys.*, 31(3):566-572.

Ye Y, J Zhu and G Wang, "Geometrics Studies on Variable Radius Spiral Cone-Beam Scanning," 2004b, *Med. Phys.*, 31(6):1473-1480.

Ye Y, J Zhu and G Wang, "A pointwise limit theorem for filtered backprojection in computed tomography," 2003, *Med. Phys.*, 30(4):816-822.

Yu H, et al., "A backprojection-filtration algorithm for nonstandard spiral cone-beam CT with an n-PI window," 2005, *Phys. Med. Biol.*, 50:2099-2111.

Yu H, Zhao S, Ye Y, Wang G, "Exact BPF and FBP algorithms for nonstandard saddle curves," 2005, *Med. Phys.*, 32(11):3305-3312.

Yu H and G Wang, "Feldkamp-type VOI reconstruction from super-short-scan cone-beam data," 2004, *Med. Phys.*, 31(6):1357-1362.

Zhao S, Yu H, Wang G, "A unified framework for exact cone-beam image reconstruction formulas," 2005, *Med Phys*, 32:1712-1721.

Zhao S., et al., "A family of analytic algorithms for cone-beam CT," 2004, *Proceedings of SPIE Developments in X-Ray Tomography IV*, 5535:318-328.

Zhao SY and G Wang, "Feldkamp-type cone-beam tomography in the wavelet framework," 2000, *IEEE Trans. Med. Imaging*, 19:922-929.

Zhou YQ, FS Foster, et al., "Applications for multifrequency ultrasound biomicroscopy in mice from implantation to adulthood," 2002, *Physiol. Genomics*, 10(2):113-126.

Zhuang T, "Fan-beam and cone-beam image reconstruction via filtering the backprojection image of differentiated projection data," 2004, *Physics in Medicine and Biology*, 49:5489-5503.

Zou Y, et al., "An extended data function and its generalized backprojection for image reconstruction in helical cone-beam CT," 2004a, *Phys. Med. Biol.*, 49:N383-N387.

Zou Y and X Pan, "Exact image reconstruction on PI lines from minimum data in helical cone-beam CT," 2004b, *Phys. Med. Biol.*, 49:941-959.

* cited by examiner (a)  (b)  (c)  (d)

SYSTEMS AND METHODS OF NON-STANDARD SPIRAL CONE-BEAM COMPUTED TOMOGRAPY (CT)

CROSS REFERENCE TO RELATED PATENT APPLICATION

This application claims priority to U.S. Provisional Application No. 60/588,682, filed Jul. 16, 2004, which is herein incorporated by reference.

ACKNOWLEDGEMENT

This invention was made partially with government support under NIH/NIBIB, Oct. 01, 2003-Sep. 30, 2008 (EB002667) and Apr. 01, 2004-Mar. 31, 2008 (EB004287). The government has certain rights in the invention.

BACKGROUND

A. Field of Invention

This invention generally relates to tomographic imaging systems and methods for exact reconstructing three/four dimensional (volumetric/dynamic) images from the data obtained in a non-standard scan, such as a non-standard spiral or non-standard saddle or a general piecewise smooth scan.

B. Description of Prior Art

Cardiovascular diseases (CVDs) are pervasive (American Heart Association 2004). CVD is the number one killer in the western world. The cost of the health care for CVD is skyrocketing. In 2004, the estimated direct and indirect cost of CVD was $368.4 billion.

Coronary artery disease is a leading cause of death as a result of a myocardial infarct (heart attack) without any symptom. Because of its ultra high temporal resolution, electron-beam CT (EBCT) can quantify calcification in the arteries, which is an indication of atherosclerosis. EBCT scanners are now considered instrumental for detecting early heart diseases and are a centerpiece of preventive cardiology programs.

Just as tomographic equipment is needed in patient studies, micro-tomographic devices are needed in small animal studies. In order to understand etiology and pathogenesis of CVD, such as high blood pressure, coronary artery diseases, congestive heart failure, stroke and congenital cardiovascular defects, as well as to develop effective prevention and treatment strategies, small animals have become some of the most common models of human diseases.

Although there has been an explosive growth in the development of micro-CT scanners, there has been no development of a micro-CT scanner that allows ultra fast in vivo imaging to study dynamic processes in high spatial and contrast resolution. As a primary example, prior to the present invention, cardiac micro-CT of the mouse was simply impossible.

In order to use these animal models fully and explore their phenotypes at the whole organ and whole animal levels, the extension of cardiovascular imaging and physiological methodologies to small animals, such as mice and rats, is imperative.

Over the last thirty years, computer tomography (CT) has gone from image reconstruction based on scanning in a slice-by-slice process to spiral scanning. From the mid 1980s to present day, spiral type scanning has become the preferred process for data collection in CT. Under spiral scanning a table with the patient continuously moves through the gantry while the source in the gantry is continuously rotating about the table. At first, spiral scanning used a one-dimensional detector array, which received data in one dimension (a single row of detectors). Later, two-dimensional detectors, where multiple rows (two or more rows) of detectors sit next to one another, were introduced. In CT there have been significant problems for image reconstruction especially for two-dimensional detectors.

For three/four-dimensional (also known as volumetric/dynamic) image reconstruction from the data provided by a spiral scan with two-dimensional detectors, there are three known groups of algorithms: Exact algorithms, approximate algorithms, and iterative algorithms. While the best approximate algorithms are of Feldkamp-type, the state of the art of the exact algorithms is the recently developed Katsevich algorithm.

Under ideal circumstances, exact algorithms can provide a replication of a true object from data acquired from a spiral scan. However, exact algorithms can require a larger detector array, more memory, are more sensitive to noise, and run slower than approximate algorithms. Approximate algorithms can produce an image very efficiently using less computing power than exact algorithms. However, even under typical circumstances they produce an approximate image that may be similar to but still different from the exact image. In particular, approximate algorithms can create artifacts, which are false features, in an image. Under certain circumstances these artifacts can be quite severe.

To perform the long object reconstruction with longitudinally truncated data, the spiral cone-beam scanning mode and a generalized Feldkamp-type algorithm were proposed by Wang and others in 1991. However, the earlier image reconstruction algorithms for that purpose are either approximate or exact only using data from multiple spiral turns.

In 2002, an exact and efficient method was developed by Katsevich, which is a significant breakthrough in the area of spiral cone-beam CT. The Katsevich algorithm is in a filtered-backprojection (FBP) format using data from a PI-arc (scanning arc corresponding to the PI-line and less than one turn) based on the so-called PI-line and the Tam-Danielsson window. The principle is that any point inside the standard spiral or helical belongs to one and only one PI-line. Any point on the PI-line can be reconstructed from filtered data on the detector plane with the angular parameter from the PI-arc. In 2003, a backprojected-filtration algorithm (BPF) was developed for helical cone-beam CT based on the Katsevich algorithm by exchanging the order of integrals. For important biomedical applications including bolus-chasing CT angiography and electron-beam CT/micro-CT, generalization of the exact cone-beam reconstruction algorithms from the case of standard spirals to the case of nonstandard spirals and other scanning loci is desirable and useful.

Although the current Katsevich-type algorithms are known for a standard spiral scan, there are no known closed-form algorithms, systems, devices and methods that can reconstruct an image exactly or quasi-exactly from data acquired in a non-standard spiral scan or a general piecewise smooth scan.

Cone-beam CT along non-standard spirals is much more flexible than standard spiral CT in biomedical imaging applications. Algorithms, systems, devices and methods are needed to achieve FBP or BPF reconstructions in non-standard spiral cone-beam scanning cases. Particularly, non-standard spiral EBCT and micro-CT systems, devices and methods are needed to facilitate dynamic volumetric imaging. Such imaging systems, devices and methods can be used in small animal and patient imaging, including cardiac imaging, bolus-chasing CT angiography, and other applications.

SUMMARY

Provided herein are methods of reconstructing an image from projection data provided by a tomography scanner that is based on geometric optics or a straight-ray model comprising scanning an object in a cone-beam imaging geometry following a general piecewise smooth scanning path or nonstandard scanning path wherein projection data is generated and an image reconstructed according to a closed-form formula. Also provided herein are systems and apparatuses for tomographic imaging.

BRIEF DESCRIPTION OF THE DRAWINGS

The accompanying drawings, which are incorporated in and constitute a part of this specification, illustrate several embodiments and together with the description illustrate the disclosed systems and methods.

DETAILED DESCRIPTION

Figure 1:
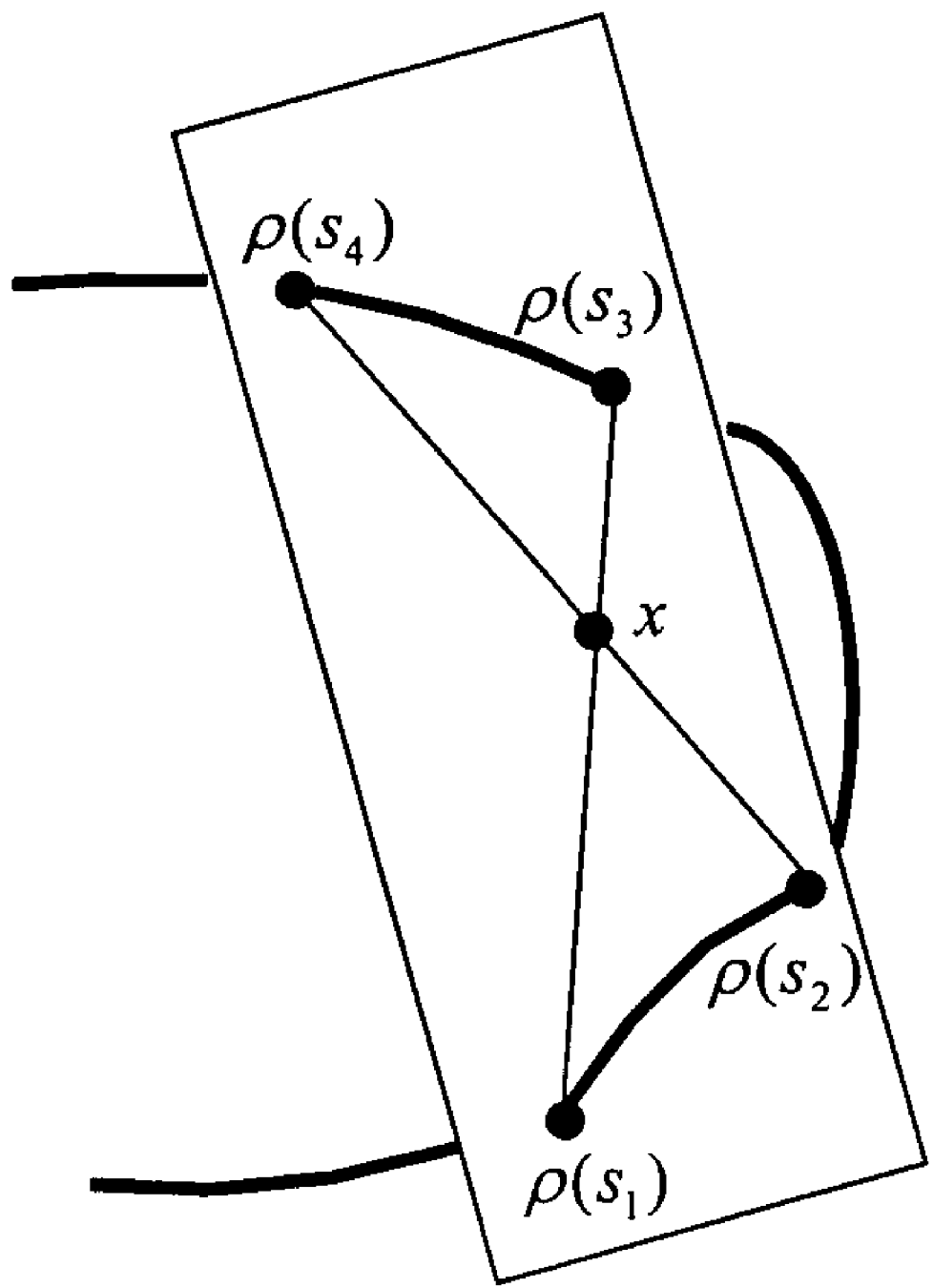
FIG. 1 shows that two PI lines, or chords, intersect if and only if their four end points on the spiral are on the same plane. There will be a point x inside the spiral with two PI lines passing through it, if there are four points on the spiral such that the four points are coplanar. Some appropriate inequalities with respect to the spiral angular parameter range must be satisfied to let the first and third points be within one turn, and the second and fourth points also within one turn, which are a condition for PI lines. The situation that there are three points on the spiral which are on the same line also needs to be excluded. When this degenerated case happens, any fourth point will be coplanar with these three collinear points, but the two corresponding PI lines intersect at a point on the spiral.

The present invention is more particularly described in the following examples that are intended as illustrative only since numerous modifications and variations therein will be apparent to those skilled in the art. As used in the specification and in the claims, "a" can mean one or more, depending upon the context in which it is used. For the purposes of the present disclosure, vectors can be indicated by bold font, however, there may be instances where a vector is not indicated by bold font. Embodiments are now described with reference to the Figures, in which like numbers indicate like parts throughout the Figures. Here and everywhere below by the phrase that the algorithm of the invention reconstructs an exact image, it will mean that in theory the algorithm is capable of reconstructing an exact image. Since in real life any data contains noise and other imperfections such as the discrete and finite nature of digital computers and data acquisition systems, no algorithm is capable of reconstructing an exact image, therefore exact and quasi-exact can be used interchangeably.

Definitions

In this specification and in the claims that follow, reference will be made to a number of terms which shall be defined to have the following meanings:

"Computer Tomography" (CT) is a powerful nondestructive evaluation (NDE) technique for producing multi-dimensional images of an object from projections (equivalent to line integrals of the underlying function).

"Filtered Backprojection" (FBP) is an image reconstruction technique wherein the cone beam data is first filtered and finally backprojected to create an image.

"Backprojected Filtration" (BPF) is an image reconstruction technique wherein the filtered cone beam data is backprojected and finally filtered to create an image.

"Electron Beam Computer Tomography," (EBCT), also known as ultra-fast computed tomography, is a CT scanner specifically developed for imaging of the heart. In the EBCT design, an electron beam is focused magnetically directed at the (such as tungsten) target. Then, the target yields a focus spot generating X-ray photons. Some of these photons penetrate a patient, and are detected by an array of detectors for use in tomographic reconstruction.

By a "subject" is meant an individual. The term subject includes small or laboratory animals as well as primates, including humans. A small animal includes, but is not limited to, a rodent such as a mouse or a rat. The term small animal is also used interchangeably with animal, laboratory animal, small laboratory animal, or subject, which includes mice, rats, cats, dogs, fish, rabbits, guinea pigs, rodents, etc. The term laboratory animal does not denote a particular age or sex. Thus, adult and newborn animals, as well as fetuses (including embryos), whether male or female, are included.

Provided herein are tomographic imaging systems and methods for reconstructing three/four dimensional (volumetric/dynamic) images exactly/quasi-exactly from cone-beam data obtained in a non-standard spiral scan or a more general piecewise smooth scan based on closed-form formulas. The method of reconstructing an image utilizes projection data provided by a tomography scanner that is based on geometric optics or a straight-ray model, such as X-ray CT, PET, and SPECT scanners. The method can generally comprise the scanning of an object in a cone-beam imaging geometry following a nonstandard scanning path (source locus or focal trajectory) or a general piecewise smooth scanning path, and reconstructing an image (such reconstruction can be via a serial and/or parallel fashion) according to a closed-form formula that is theoretically exact or quasi-exact (such as formulas in filtered-backprojection or backprojected-filtration formats, either spatially variant or invariant). Further provided herein are filtered backprojection (FBP) and backprojected filtration (BPF) algorithms for non-standard spiral CT to serve the same purpose.

The system and methods can be used in non-standard spiral cone-beam EBCT and/or nonstandard spiral cone-beam micro-CT to facilitate volumetric/dynamic imaging. The disclosed methods and systems can be used in small animal and/or patient imaging, including cardiac imaging, bolus-chasing CT angiography, and other applications not limited to the biomedical field.

Formulation

1. Non-Standard Spiral Cone-Beam Scanning

Let $$\rho(s) = (R(s)\cos s, R(s)\sin s, h(s)), \quad a \leq s \leq b, \tag{1}$$

be a nonstandard spiral with variable radius $R(s)$ and variable pitch $h(s)$. Assume that $R(s)>0$ and $h'(s)\geq 0$ in a typical case ($h'(s)<0$ can also be allowed, such as in the case of nonstandard saddle loci, as described in detail below) for any s, with b>a are appropriate constants. Assume that there is a region P inside the spiral such that for any point $r=(x, y, z)\in P$, there is at least one PI line, also referred to as a chord, of the spiral passing through r. Here a PI line is a line passing through two points $\rho(s_1)$ and $\rho(s_2)$ on the spiral, with $0<s_2-s_1<2\pi$.

Consider an object function $f(r)$ whose support is contained in P, i.e., $f(r)=0$ for any $r\notin P$. Assume that $f(r)$ is continuous and smooth. For any unit vector $\beta$, define the cone-beam projection of $f(r)$ from a point $\rho(s)$ on the spiral by $$D_f(\rho(s), \beta) = \int_0^\infty f(\rho(s) + t\beta)\,dt. \tag{2}$$

Note that this integral is actually taken over a finite interval, because the function $f(r)$ is compactly supported. When $\beta$ points away from the support of $f(r)$, the integral vanishes. In the computation below, take the unit vector $\beta$ as the one pointing to a point $r\in R^3$ from a point $\rho(s)$ on the spiral:

$$\beta(r, s) = \frac{r - \rho(s)}{|r - \rho(s)|}. \tag{3}$$

For a point $r\in P$, denote the two end points of the PI line segment by $\rho(s_1(r))$ and $\rho(s_2(r))$, where $s_1=s_1(r)$ and $s_2=s_2(r)$ are the parameters of these two points on the spiral. Define a unit vector along the PI line:

$$e_\pi(r) = \frac{\rho(s_2(r)) - \rho(s_1(r))}{|\rho(s_2(r)) - \rho(s_1(r))|}. \tag{4}$$

2. Saddle Curve Cone-Beam Scanning

A saddle curve is defined as the intersection of the two surfaces in the natural (Cartesians) coordinate system:

$$S_1 := \{(x, y, z) : z = g_1(x)\} \tag{5}$$

and $$S_2 := \{(x, y, z) : z = g_2(y)\}, \tag{6}$$

where the functions $g_1(x)$ and $g_2(x)$ satisfy $$\begin{cases} g_1''(x) > 0 \text{ everywhere} & g_1'(0) = 0, g_1(0) < 0; \\ g_2''(y) < 0 \text{ everywhere} & g_2'(0) = 0, g_2(0) = -g_1(0). \end{cases} \tag{7}$$

Define $$g_1(x) = h\left(\frac{2x^2}{R^2} - 1\right)$$

and $g_2(y)=-g_1(y)$ with constants h and R, and obtain the standard saddle curve in the cylindrical coordinate system:

$$\rho(s) := (R\cos(s), R\sin(s), h\cos(2s)), \quad s\in[0, 2\pi). \tag{8}$$

Note that the saddle curve is a periodic function of s. Its closeness makes it possible to collect data continuously over multiple periods, facilitating, for example, cardiac and other volumetric/dynamic imaging.

If h and R in (8) depend on s, $R=R(s)$ and $h=h(s)$, there is a nonstandard saddle. With $$g_1(x) = h_0\left(\frac{2x^2}{R_a^2} - 1\right) \text{ and } g_2(y) = h_0\left(1 - \frac{2y^2}{R_b^2}\right),$$

there is an elliptic saddle curve, which can be parameterized in the cylindrical coordinate system:

$$R(s) = \frac{R_a R_b}{\sqrt{R_b^2 \cos^2(s) + R_a^2 \sin^2(s)}}, \tag{9}$$

$$h(s) = h_0 \frac{R_b^2 \cos^2(s) - R_a^2 \sin^2(s)}{R_b^2 \cos^2(s) + R_a^2 \sin^2(s)} \times \frac{1}{\cos(2s)}, \tag{10}$$

where $R_a$ and $R_b$ represent the semi-axial lengths along the x- and y-axis, respectively, and $h_0$ is a constant representing the maximum longitudinal coordinate of the saddle curve.

The generalized BPF and FBP formulas disclosed herein can be applied to any piecewise smooth scanning curve, by way of example, but not limited to, non-standard spiral or saddle curves.

3. PI-Line Existence and Uniqueness, n-PI-Lines, and Chords

The existence and uniqueness of the PI-lines (or "chords" in a more general setting; in the following these two concepts "PI-line" and "chord" are used and/or interpreted exchangeably), which can also be extended to chords or n-PI-Lines, was evaluated in the nonstandard spiral case. Although the exact reconstruction does not necessarily depend on the uniqueness of the PI line (or chord), this uniqueness can minimize the redundancy in cone-beam data acquisition, and simplify the weighting function in the reconstruction process. FIG. 1 shows that two PI lines, or chords, intersect if and only if their four end points on the spiral are on the same plane. There will be a point x inside the spiral with two PI lines passing through it, if there are four points on the spiral such that the four points are coplanar. Some appropriate inequalities with respect to the spiral angular parameter range must be satisfied to let the first and third points be within one turn, and the second and fourth points also within one turn, which are a condition for PI lines. The situation that there are three points on the spiral which are on the same line also needs to be excluded. When this degenerated case happens, any fourth point will be coplanar with these three collinear points, but the two corresponding PI lines intersect at a point on the spiral.

For a standard spiral (19) of a constant radius R and pitch h, it was proved that for any point (x, y, z) inside the spiral, i.e., when $x^2+y^2<R^2$ and $a+2\pi \leq s \leq b-2\pi$, for a and b with $b-a>4\pi$ as above, there is a unique PI line passing through (x, y, z) (Danielsson et al., *Proc. of the* 1997 *Int'l Meeting on Fully Three-Dimensional Image Reconstruction in Rad. and Nuc. Med.*, (1997)). When the spiral (1) is nonstandard, however, one cannot expect to have one and only one PI line passing through any given point inside the spiral in general. One should seek two different kinds of regions inside the spiral (1). While a region of PI lines is defined as a region such that for any point in that region there is one or more PI lines passing through it, the region of unique PI lines is a region such that passing through any point in that region there is a unique PI line. Denote the former by P and the latter by U. Thus $U \subseteq P$.

The region of PI lines can be determined for a given nonstandard spiral by the union of all PI line segments:

$$P = \bigcup_{0<s_1-s_2<2\pi} \{t\rho(s_1) + (1-t)\rho(s_2) | 0 < t < 1\}. \quad (11)$$

The disclosed generalization of the exact BPF reconstruction formula is valid for any point $r \in P$. To see the redundancy in cone-beam data acquisition, assume that there are two PI lines passing through a point $r \in P$. The generalized exact BPF reconstruction formula can be applied twice. Consequently, $f(r)$ will be computed twice. This redundancy can be corrected via weighting to produce the final image.

To determine the region of unique PI lines, it can be taken into account that there is more than one PI line if and only if there are four points $\rho(s_j), j=1, \ldots, 4$, on the spiral with $s_1<s_2<s_3<s_4$, $s_3-s_1<2\pi$, and $s_4-s_2<2\pi$, such that they are on the same plane. In fact, these four co-plane points are the end points of the PI lines segments on the spiral. One should exclude the degenerated case of three end points being on the same line. This principle can be used to determine a region of unique PI lines for any given nonstandard spiral. Note that regions of unique PI lines have been determined when the spiral (1) has a variable pitch but a constant radius (Ye et al 2004b), and when the spiral has a constant pitch but a variable radius (Ye et al 2004c).

A generalized 1-PI-window at so can be defined as the region in the detector plane bounded by the cone-beam projections of the upper and lower turns of the 3D nonstandard spiral starting from the x-ray source at $y(s_0)$ in the local coordinate system. The top and bottom boundaries of the minimum detector area $\Gamma_{top}$ and $\Gamma_{bot}$ are the cone-beam projections of the upper and lower spiral turns $y_u(s_0, \lambda)$ and $y_l(s_0, \lambda)$, respectively given by $$y_u(s_0, \lambda) = y(s_0+\pi+\lambda), \text{ for } -\pi<\lambda<\pi, \quad (12)$$

$$y_l(s_0, \lambda) = y(s_0-\pi+\lambda), \text{ for } -\pi<\lambda<\pi. \quad (13)$$

Similarly, a generalized n-PI-window can be defined.

Figure 11:
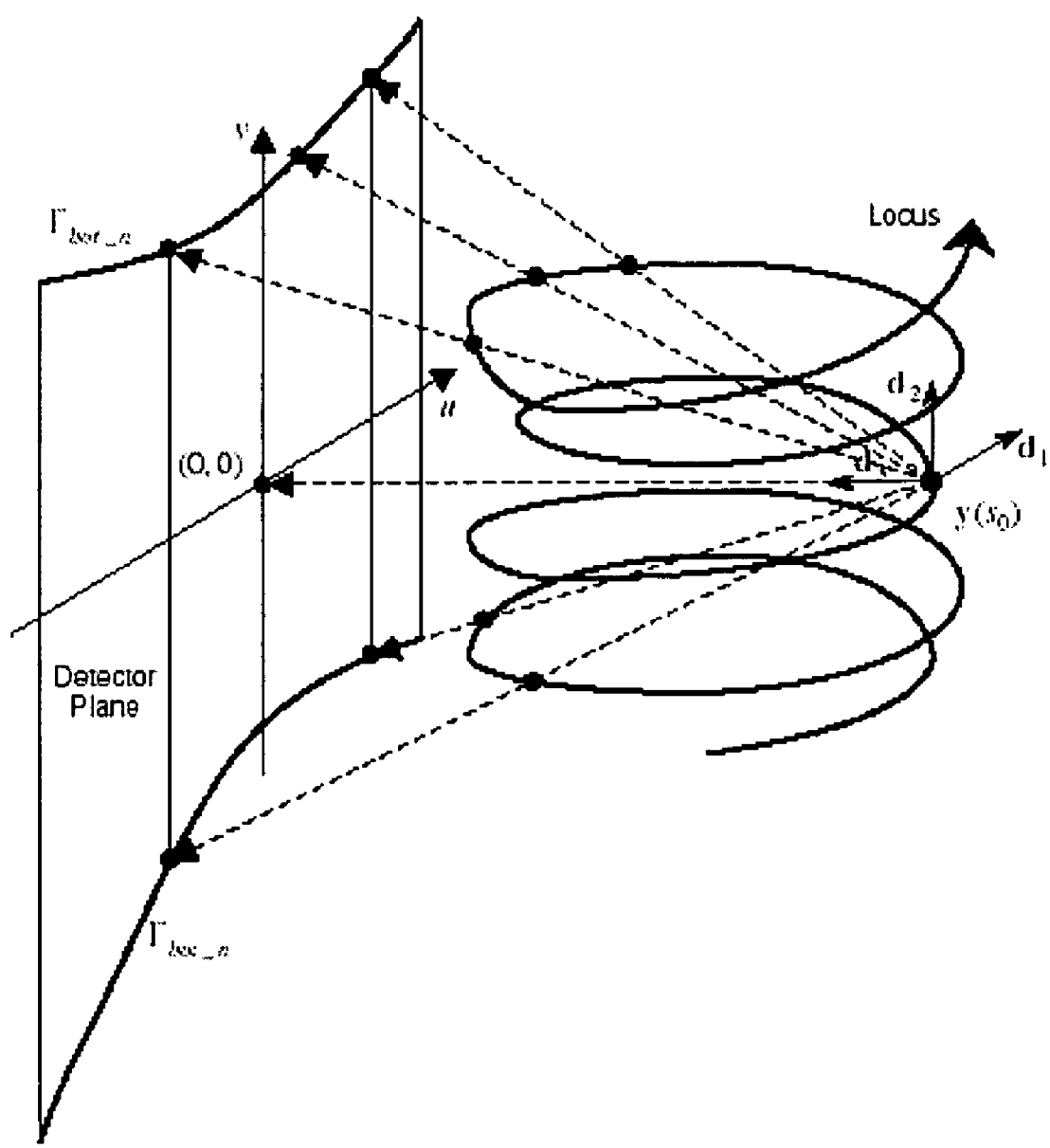
FIG. 11 illustrates a generalized 3-PI-window associated with a nonstandard spiral locus.

FIG. 11 illustrates a generalized 3-PI-window associated with a nonstandard spiral locus.

A generalized n-PI-line can be defined as any line with two points $y(s_b)$ and $y(s_t)$ on the spiral satisfying $(n-1)\pi<s_t-s_b<(n+1)\pi$. An n-PI-segment is the segment of an n-PI-line inside the spiral. Any point on the generalized n-PI-segment can be viewed from at least 180° from an appropriate viewing direction, permitting accurate and reliable reconstruction (Zhao et al 2004, Ye et al 2004a).

In a more general setting, a chord can span a trajectory for cone-beam scanning. In this case, any point on the chord should be observable from a sufficiently large angular range of cone-beam projections as required by the classic Orlov theorem, although here the beam is divergent and truncated. Exact cone-beam reconstruction is feasible in the case of rather general scanning trajectories.

4. Generalized FBP Reconstruction

The main setting is a general smooth curve y(s) for $s_b \leq s \leq s_t$, and a chord l, connecting the endpoints $y(s_b)$ and $y(s_t)$ of the curve. Let x be an interior point on l. This setting covers standard or nonstandard spirals with PI- or n-PI lines, standard or nonstandard saddle curves, and many other cases.

Following Katsevich's convention, denote by $I_{PI}(x)=[s_b, s_t]$ the parametric interval, and by $$D_f(y, \Theta) = \int_0^\infty f(y+t\Theta)dt, \Theta \in S^2, \quad (14)$$

the cone-beam data, where $S^2$ is the unit sphere. Let $$\beta(s, x) = \frac{x-y(s)}{|x-y(s)|}, s \in I_{PI}(x), \quad (15)$$

be the unit vector pointing toward x from y(s), and e(s, x) a unit vector perpendicular to $\beta(s, x)$. In the work by Katsevich, e(s, x) is selected in an explicit way. However, in the following first request that e(s, x) be any unit vector perpendicular to $\beta(s, x)$. Then, give an admissible condition for e(s, x) and make a natural choice of e(s, x). Hence, a filtering direction can be expressed by $$\Theta(s, x, \gamma) = \cos \gamma \beta(s, x) + \sin \gamma e(s, x). \quad (16)$$

The disclosed FBP approach is based on the following theorem:

Theorem 1. Let f(x) be a function of compact support whose fifth partial derivatives are absolutely integrable in $R^3$. Let e(s, x) be a unit vector satisfying condition (18) for any $s \in (s_b, s_t)$ and $x \in R^3$, or simply set e(s, x) to be a unit vector in the plane determined by l, and x-y(s) with $e(s, x) \cdot [y(s_t)-y(s_b)] > 0$. Then $$f(x) = \quad (17)$$

$$-\frac{1}{2\pi^2} \int_{I_{PI}(x)} \frac{ds}{|x-y(s)|} PV \int_0^{2\pi} \frac{\partial}{\partial q} \times D_f[y(q), \Theta(s, x, \gamma)]\Big|_{q=s} \frac{d\gamma}{\sin\gamma}.$$

The choice of e(s, x) in Theorem 1 means that the filtering plane as defined by Eq. (16) contains both l, and x-y(s) for any source point y(s).

The assumption of integrable fifth partial derivatives is much weaker than the usual condition requesting f(x) being smooth, and yet strong enough for the convergence of integrals and interchange of integration orders. As a result, distribution can be avoided in a proof. Note that in most medical and industrial applications, an object function f(x) is usually not continuous, which is a main reason for artifacts in CT images. A goal is to develop an exact reconstruction formula for discontinuous object functions. The assumption on f(x) in Theorem 1 can contribute to that goal.

Equation (17) was proved by Katsevich in the standard helical scanning case with his choice of the filtering direction $\Theta(s, x, \gamma)$. Theorem 1 is valid for a much more general class of scanning loci and filtering directions or planes.

$e(s_j, x)$ can be selected so that the following condition is satisfied:

$$\sum_{j=0}^{r} sgn[v \cdot y'(s_j)] sgn[v \cdot e(s_j, x)] = 1 \quad (18)$$

for any $v \in R^3$, where $s_j$ depends on v as described above. Equation (18) is the general admissible condition for selection of filtering directions. $s_j$ are solutions of $v \cdot [x-y(s)]=0$ for a given $v \in R^3$. Thus, x and $y(s_j)$, $0 \leq j \leq r$, are on a plane perpendicular to v.

One natural choice of e(s, x) satisfying Eq. (18) is as follows. Take e(s, x) in the direction of the projection of the vector $y(s_t)-y(s_b)$ on the plane $\Pi$ perpendicular to x-y(s). With this choice of e(s, x), one has:

$$sgn[v \cdot e(s_j, x)] = sgn\{v \cdot [y(s_t) - y(s_b)]\}$$

for all $v \in \Pi$, i.e., for all $v \in R^3$ with $v \cdot [x-y(s_j)]=0$. Thus, $$\sum_{j=0}^{r} sgn[v \cdot y'(s_j)] sgn[v \cdot e(s_j, x)] = sgn\{v \cdot [y(s_t) - y(s_b)]\} \sum_{j=0}^{r} sgn[v \cdot y'(s_j)].$$

$v \cdot [y(s_t)-x]$ and $v \cdot [y(s_b)-x]$ are of opposite signs, and hence $$\sum_{j=0}^{r} sgn[v \cdot y'(s_j)] = sgn\{v \cdot [y(s_t) - y(s_b)]\}.$$

This selection of e(s, x) can be expressed more explicitly. Note that e(s, x) is in the direction of the projection of the vector $y(s_t)-y(s_b)$ on the plane $\Pi$ perpendicular to x-y(s). Therefore, e(s, x) is in the plane determined by the line l, and the vector $$\beta(s, x) = \frac{[x - y(s)]}{|x - y(s)|}.$$

The choice of filtering planes, as given by Eq. (16), is therefore always the planes set by l, and x-y(s).

5. Generalized BPF Reconstruction

A BPF formula for exact image reconstruction for cone-beam CT along a standard spiral $$\rho(s) = (R \cos s, R \sin s, sh/(2\pi)), \quad a \leq s \leq b, \quad (19)$$

was proposed (Y. Zou and X Pan, *Phy. in Med. and Biol.*, (2004)). Here R is a constant radius, and h is a constant pitch. This standard spiral has a standard Tam-Danielsson window (Tam, et al., *Phys. Med. Biol.*, (1998) and Danielsson et al., *Proc. of the 1997 Int'l Meeting on Fully Three-Dimensional Image Reconstruction in Rad. and Nuc. Med.*, (1997)) on a detection plane. Zou and Pan's approach for the derivation of their formula uses geometry of the standard spiral and its Tam-Danielsson window, and was not generalized to the general case of nonstandard spirals.

The formulas disclosed herein are not restricted to the standard geometry of the spiral and its associated Tam-Danielsson window, and can support exact image reconstruction with cone-beam scanning along nonstandard spirals with variable radii and variable pitches, along standard and nonstandard saddle curves, as well as other scanning trajectories.

First define an integral kernel $$K(r, r') = \frac{1}{2\pi i} \int_{R^3} sgn(v \cdot e_\pi(r)) e^{2\pi i v \cdot (r-r')} dv. \quad (20)$$

The integral in (20) diverges in the ordinary sense, and hence K(r, r') is interpreted as a distribution. In this application, distributions are not used in the computation. Therefore, the meaning of K(r, r') is that it defines an integral transform from a function g on $R^3$ to $$\int_{R^3} K(r, r') g(r') dr' = \quad (21)$$

$$\frac{1}{2\pi i} \int_{R^3} sgn(v \cdot e_\pi(r)) e^{2\pi i v \cdot r} dv \int_{R^3} g(r') e^{-2\pi i v \cdot r'} dr'.$$

In other words, the integral transform on the left side of (21) is by definition a twisted Fourier inverse transform of the Fourier transform of g. Given an object function $f(r)$ of compact support in P, let us consider a special function g which is given by following expression $$g(r') = \quad (22)$$

$$\int_{s_1(r)}^{s_2(r)} \frac{\partial}{\partial q} (D_f(\rho(q), \beta(r', s)) - D_f(\rho(q), -\beta(r', s))) \Big|_{q=s} \frac{ds}{|r' - \rho(s)|}.$$

Note that, because of the upper and lower limits $s_2(r)$ and $s_1(r)$, the function g(r') also depends on $r \in P$. g(r') is the weighted cone-beam backprojection of the derivative of the filtered data for the point $r \in P$ (Y. Zou and X Pan, *Phy. in Med. and Biol.*, (2004)). It is the subject matter of Zou and Pan that one can recover $f(r)$ by applying the integral transform (21) to g(r') in (22), for cone-beam projections along a standard spiral (19) (Y. Zou and X Pan, *Phy. in Med. and Biol.*, (2004)). In other words, they formulated (23) below for the standard spiral (19). The subject matter of this invention involves (23) for nonstandard spirals (1), and applies to other smooth curves as well, for example, standard and nonstandard saddle curves.

Theorem 2. Consider a nonstandard spiral (1) with a region P of PI lines. Let $f(r)$ be a function of compact support in P, whose 5th partial derivatives are absolutely integrable in $R^3$. Then $$f(r) = \int_{R^3} K(r, r')g(r')dr', \qquad (23)$$

where the integral transform is defined in (8), g(r') is given by (22), $D_f(\rho(q),\beta(r', s))$ by (2), and $\beta(r, s)$ by (3).

In Theorem 2 it may be simply assumed that $f(r)$ is a smooth function of compact support in P, and hence all its partial derivatives exist and are continuous. The disclosed generalized BPF reconstruction formulation applies to a quite general class of scanning loci, including but not limited to nonstandard spirals defined by (1). Actually, as long as r is on a line segment and $\rho(s)$ is a smooth curve running from one endpoint $\rho(s_1(r))$ on the line segment to the other endpoint $\rho(s_2(r))$ also on that segment, Eq. (23) holds. The generalized BPF formula can be applied to cone-beam scanning along a saddle curve as in Pack et al., *Proc. of the VIIth Int'l Conf on Fully 3D Reconstruction In Rad. and Nuc. Med.*, (2003), or more generally, to cone-beam scanning along a nonstandard curve, including saddles and spirals. Theorem 2 enables an exact reconstruction of $f(r)$ if its support is contained in a region P of PI-Lines. If the region P does not completely cover the support of $f(r)$, the theorem is still applicable for the exact reconstruction inside the region P.

Algorithms

Both FBP and BPF cone-beam algorithms have been developed and implemented for exact image reconstruction and are herein described in the nonstandard spiral case as an example.

I. Filtered Backprojection (FBP)

The generic Katsevich algorithm was formulated in the FBP format. As described herein, it has been generalized for nonstandard spiral cone-beam CT comprising, calculating derivatives of projection data with respect to a source position, determining at least one PI-line or a chord that passes through the object to be reconstructed, performing slant filtration on derivatives of the projection data, generating filtered data, and performing weighted backprojection of the filtered data, generating backprojected data.

Figure 3:
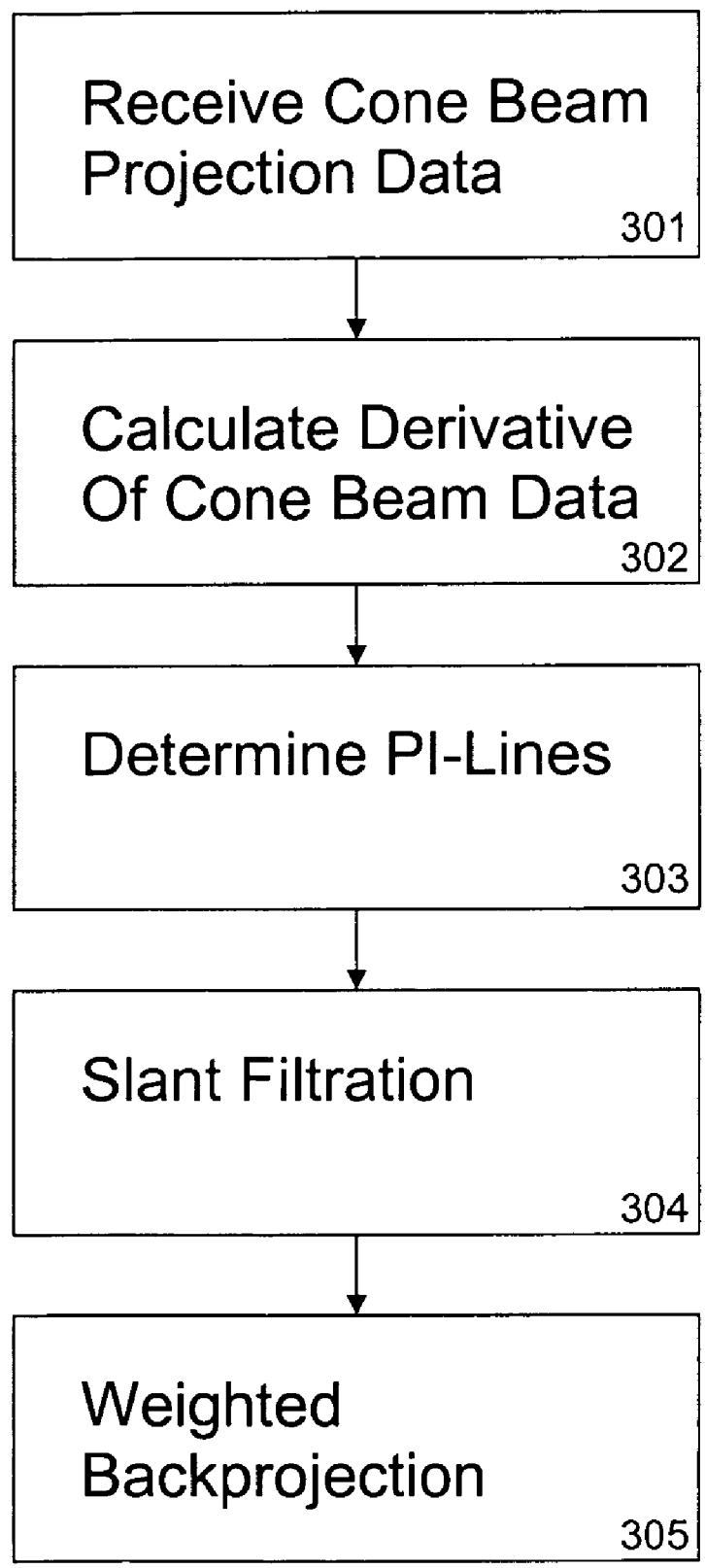
FIG. 3 shows the general process of the Non-Standard Spiral Filtered Backprojection (FBP) reconstruction algorithm.

Such a generalized algorithm can comprise the following processes, as shown in FIG. 3 and as described below. As shown in 301 cone beam projection data can be received. In 302, the derivative of cone beam data can be calculated. In 303 the PI-lines can be determined. In 304, slant filtration can be implemented. In 305, weighted backprojection can be performed.

a) Cone-Beam Data Differentiation.

Keeping $\beta$ intact and using the chain rule, the derivative of cone-beam data with respect to s can be written as $$G(s, u, v) \equiv \frac{d}{ds}g(s, u, v)\bigg|_{\beta\ fixed} = \qquad (24)$$

$$\left(\frac{\partial}{\partial s} + \frac{R'(s)u + u^2 + D^2(s)}{D(s)}\frac{\partial}{\partial u} + \frac{R'(s)v + uv}{D(s)}\frac{\partial}{\partial v}\right)g(s, u, v)$$

To compute the derivatives, a finite difference formula can be used (Noo, et al., *Phy. in Med. and Bio.*, (2003).

b) PI-Line Determination.

Assume the nonstandard spiral locus satisfies the conditions for existence and uniqueness of the PI-line, the following procedure can be used to determine the PI segment $I_{PI(x)}$ for any given point $x \in U$. Let the two ends of the PI segment $I_{PI(x)}$ be $s_b(x)$ and $s_t(x)$. There must be a unique triplet $s_b$, $s_t$, and t with $t \in (0,1)$ and $0 < s_t - s_b < 2\pi$ such that $x = ty(s_b) + (1-t)y(s_t)$. First, consider a family of the PI-lines intersecting the vertical line V containing x. This family of PI-lines can be parameterized by $s_b$. Through a fixed $y(s_b)$, one can numerically find the PI-line that intersects the line V and $y(s_t)$ with $s_t \in (s_b, s_b + 2\pi)$. Because the longitudinal coordinate of such an interaction is an increasing function of $s_b$, using dichotomy one can numerically identify the unique $s_b$ and $s_t$ so that $I_{PI(x)}$ contains $x \in U$.

c) Slant Filtration.

The generic Katsevich algorithm uses a slant filtering on the detector plane. In the standard helical scanning case, the involved filtering lines are independent of the source position. However, in the nonstandard spiral scanning case, the filtering paths depend on the source, detector and object locations. Following processes similar to that for the implementation of the generic Katsevich algorithm, the equation for filtering paths can be obtained, which has to satisfy the following general admissible condition:

$$\sum_{j=0}^{r} sgn[v \cdot y'(s_j)]sgn[v \cdot e(s_j, x)] = 1, \qquad (25)$$

which is a repetition of Eq. (18).

d) Weighted Backprojection.

The filtered data at different source positions within the PI interval contribute to the reconstruction at x according to weight inversely proportional to the distance from x to the source y(s). The detector area required in the Katsevich-type reconstruction can be larger than the extended Tam-Danielsson window depicted by the projected upper and lower spiral half turns. This process is the same as that used in the generic Katsevich algorithm (i.e., backprojection is done along the true ray paths according to weight inversely proportional to the distance from x to the source y(s)). The proposed Katsevich-type formula with the nonstandard spiral locus allows exact reconstruction from truncated cone-beam data as defined by the extended Tam-Danielson window.

II. Backprojection Filtration (BPF)

Recently, Zou and Pan reformulated the generic Katsevich algorithm into a BPF counterpart in the standard spiral (helical) cone-beam geometry (Y. Zou and X. Pan, Phys. in Med. and Biol., (2004)). As described herein, it has been developed into a generalized BPF algorithm for nonstandard spirals and other curves, for example, variable radius spiral cone-beam CT/micro-CT. As described herein, it has been generalized for nonstandard spiral cone-beam CT comprising, calculating derivatives of projection data with respect to a source position, determining at least one PI-line or a chord that passes through the object to be reconstructed, performing weighted backprojection of derivatives of the projection data onto a PI-line or a chord, generating backprojected data, and performing an Inverse Hilbert Transform on the backprojected data along the PI-line or a chord, generating transformed data. Optionally, a further step of rebinning can be performed on the transformed data.

Figure 4:
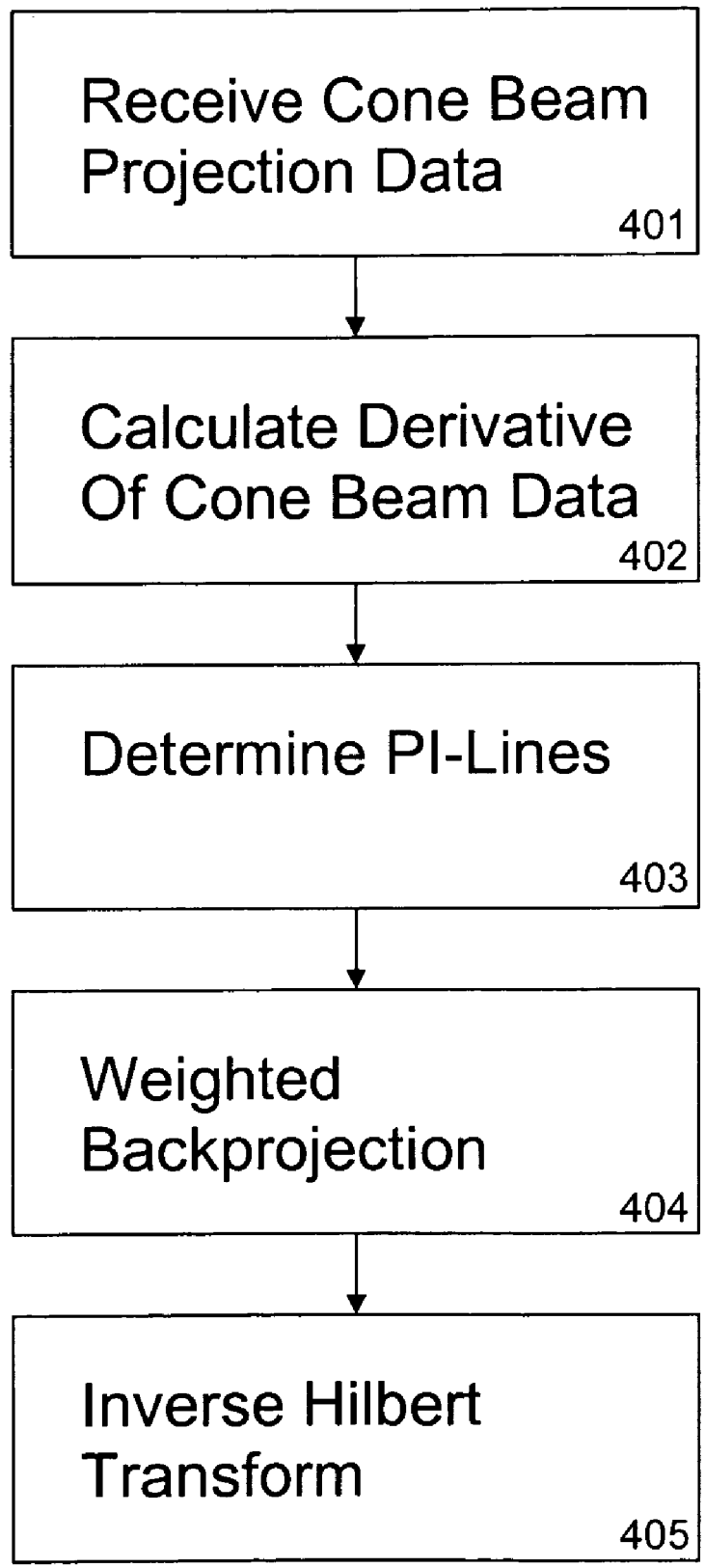
FIG. 4 shows the general process of the Non-Standard Spiral Backprojected Filtration (BPF) reconstruction algorithm.

Such a generalized algorithm can comprise the following processes, as shown in FIG. 4 and as described below. As shown in 401 cone beam projection data can be received. In 402, the derivative of cone beam data can be calculated. In 403 the PI-lines can be determined. In 404, weighted backprojection can be performed. In 405, inverse Hilbert transform can be applied. The key algorithmic processes are as follows:

a) Cone-Beam Data Differentiation.

The operations are the same as in the preceding FBP description.

b) PI-Line Determination.

The operations are the same as in the preceding FBP description.

c) Weighted Backprojection.

Calculate the weighted 3D backprojection p(x') of the cone-beam data derivatives onto a fixed PI-line segment $I_{PI(x)}$:

$$p(x') = \int_{s_t(x)}^{s_b(x)} \frac{G(s, \tilde{u}, \tilde{v})}{|x' - y(s)|} ds \quad (26)$$

with $$\tilde{u} = \frac{D(s)(x' - y(s)) \cdot d_1}{(x' - y(s)) \cdot d_3}, \tilde{v} = \frac{D(s)(x' - y(s)) \cdot d_2}{(x' - y(s)) \cdot d_3} \quad (27)$$

In fact, one only need calculate the values of p(x') at discrete sampling points. Hence, one may denote the value of p(x') as p($\tilde{x}_l$), where l=0,1, ... L−1, L indexing the data along the axis $\tilde{x}$ that is coincident with the PI-line.

Furthermore, the weighted 3D backprojection $g_\pi(x_{\pi 1}, s_b, s_t)$ of the derivatives of cone-beam data can be calculated onto an n-PI-segment specified by $s_b$ and $s_t$ using equations (22) and (37). Note that there may be a number of n-PI-lines through a given point inside the object. Hence, multiple reconstructions may exist at that point. When there are m n-PI-lines passing through the point x, one can select any of the n-PI-lines and the corresponding arc to reconstruct f(x). This will lead to the exact reconstruction in the case of noise-free cone-beam data. In the case of noisy data, the reconstruction can be performed m times to utilize the data redundancy for noise reduction.

d) Inverse Hilbert Transform.

Using the same formula by Zou and Pan, one has $$p(\tilde{x}) = 2 \int_{\tilde{x}_b}^{\tilde{x}_t} \frac{f(\tilde{x})}{\tilde{x} - \tilde{x}'} d\tilde{x}' \quad (28)$$

where [$\tilde{x}_b$, $\tilde{x}_t$] covers the PI segment $I_{PI(x)}$ (Y. Zou and X. Pan, *Phys. in Med. and Biol.*, (2004)). This relationship can be put in a matrix form linking p($\tilde{x}_l$) and f($\tilde{x}_l$) at the discrete sampling points along the axis $\tilde{x}$. Then, one can invert the system to obtain f($\tilde{x}_l$). As would be clear to one skilled in the art, there are alternative ways for performing this step. By way of example, and not limitation, assume that f(t) is compactly supported on [a, b], its Hilbert transform is given by:

$$g(t) = f(t) * \left(\frac{1}{\pi t}\right) = \int_a^b \frac{f(t')}{\pi(t-t')} dt', \quad (29)$$

where the star "*" signifies a convolution operator and the singularity at t−t'=0 is treated in the Cauchy principle value sense. Although f(t) is finitely supported, g(t) exists in an infinite interval. Here recover f(t) from g(t) on a finite interval [a', b'] and [a, b] ⊂ [a', b'].

The solution to the integration equation (29) is shown as $$f(t) = \frac{-1}{\sqrt{(t-a')(b'-t)}} \left( \int_{a'}^{b'} \frac{\sqrt{(t'-a')(b'-t')} g(t')}{\pi(t-t')} dt' + C \right), \quad (30)$$

where C is a constant. The constant can be determined using a priori knowledge that f(t)=0 in [a', a] and [b, b']. Evaluating using the ray sum along the PI-line, can be expressed as $$C = -\frac{1}{\pi} \int_a^b f(t) dt. \quad (31)$$

To perform the inverse Hilbert Transform, g(t) is first discretized as $$g(k)=g(a'+k\delta+0.5\delta), k=0,1,2, \ldots K-1, \quad (32)$$

where δ=(b'−a')/K. Then, the formula (30) can be implemented in the following four steps:

Step 1: Pre-weighting: $\tilde{g}(k) = \delta \cdot g(k) \cdot \sqrt{(k+0.5)(K-k-0.5)}$;

Step 2: Hilbert Transform:

$$\overline{f}(k) = \sum_{k'=0}^{K-1} \frac{\tilde{g}(k')}{\pi(k-k')};$$

Step 3: Level-shifting: $\tilde{f}(k) = \overline{f}(k) + C$ (using (31));

Step 4: Post-weighting:

$$f(k) = \frac{\tilde{f}(k)}{\delta \cdot \sqrt{(k+0.5)(K-k-0.5)}}.$$

f(k) is the sampling value of f(t) at t=a'+kδ+0.5δ.

Rebinning

Both the FBP and the BPF methods disclosed can comprise a further step of rebinning in order to remap the reconstructed image from the chord-based coordinate system into a global coordinate system, using an appropriate interpolation method as known in the art.

Rebinning is sorting 3-D data into a stack of ordinary 2-D data sets, where for each transaxial slice the 2-D data are organized as a sinogram. These rebinned data are equivalent geometrically to conventional 2-D data and can therefore be reconstructed by applying a 2-D reconstruction algorithm to each slice separately. Thus, rebinning decomposes the 3-D reconstruction problem into a set of independent 2-D Radon transforms.

According to the above descriptions, both the BPF and FBP algorithms perform reconstruction in the chord-based coordinate system. In practice applications, an additional step can be performed to represent the reconstructed image in the natural coordinate system. This can be accomplished by determining the chord for any grid point in the hull of a nonstandard saddle curve. In the following the rebinning procedure will be described towards saddle curves, however, the principles can be generalized for nonstandard spirals and other curves.

Every point inside the hull H belongs to at least two chords (also referred to as PI-lines). To find a chord containing a fixed point $(x_0, y_0, z_0)$ in H, first consider a special plane $x=x_0$. In this case, there are two intersection points between the plane and the saddle curve. Solving the equation $R(s)\cos(s)=x_0$, obtain the view angles $\omega_1$ and $\omega_3$ that correspond to the two intersection points $W_1$ and $W_3$. On the other hand, consider another special plane $y=y_0$. Solving the equation $R(s)\sin(s)=y_0$, results in the view angles $\omega_2$ and $\omega_4$ corresponding to the two more intersection points $W_2$ and $W_4$. For an elliptic saddle curve, one has $$\omega_1 = -\cos^{-1}\left(\frac{R_a x_0}{\sqrt{R_a^2 R_b^2 + x_0^2(R_a^2 - R_b^2)}}\right), \omega_3 = -\omega_1. \quad (33)$$

$$\omega_2 = -\sin^{-1}\left(\frac{R_b y_0}{\sqrt{R_a^2 R_b^2 - y_0^2(R_a^2 - R_b^2)}}\right), \omega_4 = \pi - \omega_2. \quad (34)$$

The above four angles satisfy $\omega_1 < \omega_2 < \omega_3 < \omega_4$.

Now, consider a chord $L_\pi$ intersecting with the line $L_z$ parallel to the z-axis and containing the point $(x_0, y_0, z_0)$. In the X-Y plane, the projection of the line $L_z$ is the point $(x_0, y_0)$ and the projection of $L_\pi$ passes through the point $(x_0, y_0)$. According to the definition of a saddle curve, the line $\overline{W_1 W_3}$ intersects $L_z$ at $(x_0, y_0, g_1(x_0))$ while $\overline{W_2 W_4}$ intersects $L_z$ at $(x_0, y_0, g_2(y_0))$. The hull $H:=\{(x, y, z)|g_1(x)<z<g_2(y)\}$, hence $g_1(x_0)<z_0<g_2(y_0)$. When the starting point $W_b$ of $L_\pi$ moves from $W_1$ to $W_2$ smoothly, the corresponding end point $W_t$ will change from $W_3$ to $W_4$ smoothly, and the z-coordinate of its intersection with $L_z$ will vary from $g_1(x_0)$ to $g_2(y_0)$ continuously. Therefore, there exists at least one chord $L_\pi$ that intersects $L_z$ at $(x_0, y_0, z_0)$ and satisfies $s_{b1} \in (\omega_1, \omega_2)$, $s_{t1} \in (\omega_3, \omega_4)$. This chord can be numerically determined as follows:

Step 1: Set $s_{bmin}=\omega_1$, $s_{bmax}=\omega_2$;

Step 2: Set $s_{b1}=(s_{bmax}+s_{bmin})/2$ and find $s_{t1} \in (\omega_3, \omega_4)$ so that $\overline{\rho(s_{b1})\rho(s_{t1})}$ intersects $L_z$ by solving the equations:

$$\begin{cases} \frac{R^2(s_{t1})\cos^2(s_{t1})}{R_a^2} + \frac{R^2(s_{t1})\sin^2(s_{t1})}{R_b^2} = 1 \\ \frac{R(s_{t1})\cos(s_{t1}) - x_0}{R(s_{b1})\cos(s_{b1}) - x_0} = \frac{R(s_{t1})\sin(s_{t1}) - y_0}{R(s_{b1})\sin(s_{b1}) - y_0} \end{cases} ; \quad (35)$$

Step 3: Compute $z'$ of the intersection point between $\overline{\rho(s_{b1})\rho(s_{t1})}$ and $L_z$;

Step 4: If $z'$ is greater than $z_0$, set $s_{bmax}=s_{b1}$, and go to Step 2; if $z'$ is less than $z_0$, set $s_{bmin}=s_{b1}$, and go to Step 2; if $z'$ is equal to $z_0$, stop.

After the chord interval $(s_{b1}, s_{t1})$ is obtained using the above procedure, one can immediately obtain the other chord interval $(s_{t1}, s_{b1}+2\pi)$ since the saddle curve is closed. The union of the two intervals yields a $2\pi$ scan range. Similarly, one can find $s_{b2} \in (\omega_2, \omega_3)$ and $s_{t2} \in (\omega_4, \omega_1+2\pi)$ as well as the chord intervals $(s_{b2}, s_{t2})$ and $(s_{b2}, s_{t2}+2\pi)$. Hence, reconstruction can be performed four times for a given point in the hull of a saddle curve. Once a chord and its interval $(s_b, s_t)$ are determined for a point r in the natural coordinate system, one can estimate the reconstruction value at r by the following interpolation routine:

Step 1: Determine the adjacent points $s_{bb}$ and $s_{bt}$ of $s_b$ on the discrete grid;

Step 2: Among all the chords from the X-ray source position $\rho(s_{bb})$, find the one $L_{90}$ $(s_{bb}, r)$ with the minimum distance to r, and compute the value $\hat{f}(r_b)$ at the projection point $r_b$ of r on $L_\pi(s_{bb}, r)$ via linear interpolation;

Step 3: Compute the value $\hat{f}(r_t)$ at the projection point $r_t$ of r on $L_\pi(s_{bt}, r)$ similar to Step 2;

Step 4: Estimate $\hat{f}(r)$ from $\hat{f}(r_b)$ and $\hat{f}(r_t)$ via linear interpolation.

Electron Beam Micro CT System and Apparatus

Generally, EBCT scanners can take cross-sectional images so quickly that the beating heart can be virtually frozen. In an EBCT scanner, a sufficient amount of fan-beam projection data is acquired within 50-100 ms, which is extremely difficult to achieve using a mechanically rotated X-ray source as commonly encountered in the third and fourth generation CT scanners. By its unique physical design, the EBCT scanner dynamically steers an X-ray source spot by sweeping an electron-beam on a tungsten arc with multiple tracks, based on the same principles of a cathode ray tube in which the electron-beam is controlled by dedicated coils. Despite its undisputable advantages, current EBCT techniques are subject to at least two major weaknesses. First, it is not in cone-beam geometry and does not support standard and nonstandard spiral scanning. Second, the X-ray spot is not sufficiently intense to produce the image quality characteristic with mechanical rotation based scanners.

Just as various tomographic imaging systems are needed for patient studies, there is also a need microtomographic devices for small animal studies. Although there has been growth in the development of micro-CT scanners, much of such efforts have been dedicated to improve spatial resolution instead of temporal resolution. Since the 1990s a large number of micro-CT systems have been constructed. Most of them employ CCD cameras and micro-focus x-ray tubes to produce image resolution from a few μm to hundreds of μm. In modern micro-CT systems, the data acquisition system rotates about an animal table, while in earlier systems an animal stage is rotated in a fixed data acquisition system. These imaging systems permit screening of small animals for mutations or pathologies, and monitoring disease progression and response to therapy. However, currently an X-ray micro-CT scanner takes at least 20 seconds to acquire a full dataset. To date there is little effort for development of an ultra fast micro-CT scanner to study dynamic processes in small animals.

The methods disclosed herein can be practiced on any CT system. An example of a CT system and apparatus capable of implementing the methods is provided. The micro-CT source design can be performed based on a steerable electron-beam. In that framework, a curvilinear tungsten material or target can be arranged along a non-standard curve to be traced by an electro-magnetically driven electron-beam for formation of an X-ray source and collection of cone-beam data. Such a closed scanning geometry is advantageous for imaging a longitudinally limited volume of interest, for example, the beating heart of a mouse or rat.

Figure 8:
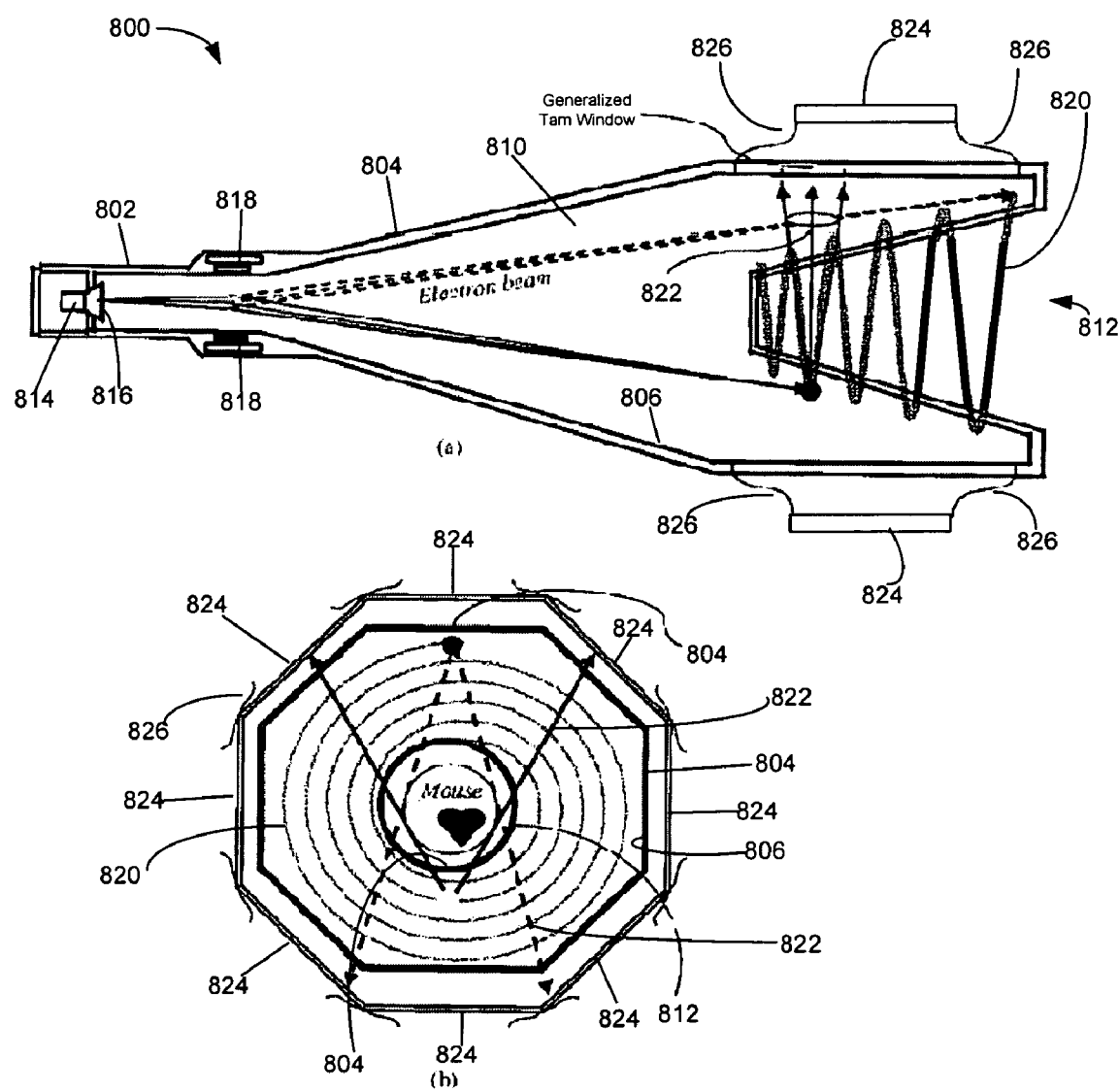
FIGS. 8(a & b) show an exemplary electron-beam micro-CT (EBMCT) device in a longitudinal cross-section view (a) and in a transverse cross-section view (b).

An exemplary electron beam CT/micro-CT scanning device 800 is shown in FIG. 8 (*a* and *b*). The side view (a) emphasizes the geometry between the charged particle beam generator 814 and the target locus 820. The cross-sectional view is seen from the perspective of the incoming electron beam. Such an imaging apparatus 800 comprises a vacuum chamber 802 having an exterior surface 804, an underlying interior surface 806, and defines an enclosed space 810. At least a portion of the exterior surface can define or surround a subject cavity 812. The subject cavity is adapted to receive a small animal subject. For example, the subject cavity can be adapted to receive a mouse or a rat. Thus, the cavity can be adapted to receive a small animal with a body having a diameter of approximately 2.0 to 6.0 centimeters. In these cases, the corresponding size of the subject cavity would be approximately about 4 to 20 centimeters in diameter at the mid-point of the subject cavity.

The apparatus 800 further comprises a charged particle beam generator 814 having a proximal and a spaced distal end 816. The distal end 816 of the charged particle beam generator is positioned within the enclosed space 810 of the vacuum chamber. The electron beam generator can generate a flat or curved electron sheet. The electron beam generator can have a scanning speed from about 25 Hz to about 50 Hz. The apparatus can comprise a single electron beam generator or a plurality of electron beam generators (not shown).

The apparatus includes a focusing mechanism 818 adapted to selectively focus charged particles generated by the charged particle beam generator and a target 820 adapted to generate X-rays upon receipt of charged particles from the charged particle beam generator. If a plurality of electron beam generators is used, the apparatus may comprise a plurality of focusing mechanisms (not shown).

The target 820 is disposed within the enclosed space 810 of the vacuum chamber about at least a portion of the interior surface of the vacuum chamber that underlies or encloses the subject cavity 812. The target can attached or coupled to at least a portion of the interior surface 806 of the vacuum chamber that underlies or encloses the subject cavity 812 using mechanisms know to those skilled in the art. The target can be a tungsten-based structure to produce cone-beam X-Ray projections 822 in a generalized Tam window.

There are several implementation problems with electron-beam techniques. The space charge of the electron-beam becomes neutralized by the beam-generated plasma in less than a scan time. Thus, the stability of electron-beam focusing is essential. Nitrogen gas can be filled into the chamber so that the neutralization saturates before the beam reaches the active part of the target. Ion clearing electrodes can ensure that the beam can be selectively self-focusing or self-defocusing. Aberration-free focusing requires that the beam phase space satisfy a certain condition. Residual aberrations due to non-uniformities can be corrected by manipulating the boundary between the neutralized and space charge dominated sections of the beam.

Bremsstrahlung X-rays can be produced by de-accelerating electrons in a tungsten-based target (alloy containing tungsten and other appropriate metallic materials). Such an X-ray source spot can be electro-magnetically moved by steering an electron beam either continuously or in a stepping fashion. The scanning locus can be defined by the geometric arrangement of curvilinear target material. The voltage difference between the charged particle generator 814 or electron gun (ground) and the tungsten-based target 820 (positive potential) can be adjusted to be significantly softer (40-80 kVp) than that of conventional CT scanner (120-250 kVp, 4-7 mm aluminum half-value layer). The initial energies of X-rays can be calculated from the published data of X-ray spectra for various target/filter materials. A nonstandard spiral target can be implemented, and other scanning loci, like a saddle curve, can be similarly implemented. The electromagnetic deflection system can control the focal spot up to the desirable specifications. A plurality of electron sources, positioned on the same side but largely separated and magnetically masked, each of which independently scans appropriate segments of the common tungsten-based target can improve imaging performance. This can effectively refine the temporal resolution. Moreover, a flat-electron-beam can be used to hit the target at multiple locations simultaneously to reduce the scanning time further.

At the energies used for micro-CT of small animals, only about 1% of the energy from the electron beam is converted to X-rays. The rest of the energy becomes heat on the spot and propagating into adjacent areas and the vacuum housing of the system. A direct contact water cooling system can be used to remove heat quickly from the target material so that multiple spiral cone-beam scans can be performed without overheating problems.

The finite area of the X-ray focal spot causes structural details to be smeared, leading to the source blurring. Furthermore, the focus spot may be asymmetric due to the nonstandard nature of the spiral locus or target and the imperfect focusing of the electron-beam. As a result, the focal spot may vary spatially. The spot size also varies with the applied tube potential (U) and current. The size of the focus spot can be modeled by assuming that it is proportional to I and inversely proportional to $U^{3/2}$. The spot intensity distribution can be modeled in various ways, such as being circular and Gaussian. The focal spot size can be around 0.1-0.2 mm in diameter, and the high voltage supply stay within 0.1% of the nominal voltage.

In one non-limiting example, the target 820 or locus adapted to generate X-rays is substantially a non-standard curvilinear spiral in shape. In another non-limiting example, the target adapted to generate X-rays is substantially circular in shape. In yet another non-limiting example, the target adapted to generate X-rays is substantially a standard saddle curve in shape. And in a further non-limiting example, the target adapted to generate X-rays is substantially a non-standard saddle curve in shape.

The X-rays generated by the target are adapted to generate X-ray projections 822 can be in a cone beam geometry or in other geometries such as, but not limited to a fan beam geometry. The number of projections produced by the target are typically sufficient for full-scan, half-scan, or super-short-scan based image reconstruction.

The focusing mechanism 818 is positioned intermediate the charged particle beam generator 814 and the target 818 such that the charged particles generated by the charged particle beam generator can be selectively and rapidly focused on selective portions of the target 820. The focusing mechanism can comprise one or more magnetic coils to focus and deflect the electron-beam through the evacuated chamber or enclosed space along the target or to selected or desired portions of the target. Thus, magnetic coils can precisely focus and steer the electron beam through the evacuated drift tube or enclosed space of the vacuum chamber. The electron beam can strike the tungsten target at an upper left location or at another desired or selected location, and are non-standard spirally scanned over multiple spiral turns. The area detector based enclosure acquires the cone-beam data during the nonstandard spiral scan. A collimation mechanism (not shown) can be used such that the charged particles generated by the charged particle beam generator can be collimated to desirable or selected regions on the target.

The apparatus further comprises a detector 824 surrounding the target. There are a large variety of detectors that can be used in the disclosed apparatuses, systems and methods. Two representative types are a) thin-film transistors (TFT, α-Si:H) and b) mono-crystalline silicone CCD/CMOS detectors. Although their quantum efficiency is high, the readout speed of TFT detectors is generally less than 30 frames per second, rarely reaching 100 frames per second. On the other hand, the readout speed of CCD/CMOS detectors can be extremely high, such as 10,000-30,000 frames per second, and are coupled with fiber-optical tapers, resulting in low quantum efficiency. For example, the 1000 Series camera from Spectral Instruments (Tucson, Ariz.), can be used. This camera is compact, measuring 92 by 92 by 168 mm. Two, three, and four-phase architecture CCDs from Fairchild Imaging (Milpitas, Calif.), E2V (Elmsford, N.Y.), Kodak (Rochester, N.Y.), and Atmel (San Jose, Calif.) can be placed in the selected camera. The readout and digitization can use 16-bit digitizer. The pixel readout rate can be varied from 50 kHz to 1 MHz. The gain of the analog processor can be modified under computer control to compensate for the gain change of the dual slope integrator at different readout speeds. The 1000 Series system offers fully programmable readout of sub arrays and independent serial and parallel register binning. In addition, specialized readout modes, such as time delay and integration (TDI) using an internal or external time base can be used. These capabilities allow the readout of only the area of the CCD of interest at variable resolution in order to optimize image signal to noise ratio.

The detector 824 is positioned to receive X-rays generated by the target. The apparatus can also include a plurality of detectors 824 that can be located external to the enclosed space 810 surrounding the target. Each detector of the plurality can be adapted to receive X-rays generated by the X-ray generating target 820. Whether a single or a plurality of detectors are used, each detector can be integral with the wall of the vacuum chamber 802, for example the detector can be disposed between the exterior 804 and underlying interior surface 806 of the vacuum chamber, or the detector can form at least a portion of the interior and/or exterior surface of the vacuum chamber. The detector or detectors can also be located external to the enclosed space and external to or surrounding the external surface of the vacuum chamber as shown in FIG. 8b. In one non-limiting example, eight CCD detectors enclose the target to receive and transmit cone-beam data at an extremely high speed. The cameras or detectors can be configured outside the vacuum chamber, and can be cooled to reduce the detector noise.

The detector cells can be arranged in a rectangular matrix, such as from about 100 by 100 to about 1000 by 1000. One or more optical tapers can be coupled with the detectors. Thus, in a non-limiting example eight CCD detector plates can enclose the nonstandard spiral target to receive and transmit cone-beam data at an extremely high speed. The optical tapers can couple the CCD cameras for maximum coverage.

The cardiac rates of mice and rats are much higher than that of the human, as summarized in Table 3.

TABLE 3

Cardiac rates, diameters and body dimensions of the mouse and rat.

| | Heart rate | Heart diameter | Body Size |
|---|---|---|---|
| Rat | ~360 bpm = 6 bps | 15 mm | <200 × 50 mm |
| Mouse | ~600 bpm = 10 bps | 7 mm | <100 × 25 mm |

In terms of temporal resolution, the disclosed EBMCT scanner can improve EBCT by several folds to an order of magnitude and outperforms current micro-CT by several orders of magnitudes. As a representative case, assume a cardiac rate of 7 beats per second (about 5 times higher than that of the human) and 10 tomographic images per cardiac cycle. In this example, 70 tomographic images per second are needed. If the diameter of the cardiac region of a mouse is 10 mm, the area of 10 by 10 mm can be covered with 100 by 100 detector cells (100 µm detector size). To produce images of a 100 by 100 by 100 voxels, 100 cone-beam projections can be sufficiently high. According to the recent results on MRI VIPR (a magnetic resonance imaging technique using Vastly undersampled Isotropic PRojection) (Barger et al., *Magn. Reson. Med*, (2002)), even 30 cone-beam projections could be workable for adequate image quality. Assume that the diameter of the mouse thorax is 30 mm, each cone-beam view roughly consists of 300 by 300 detector cells. Therefore, the range for the number of cone-beam projections of 300 by 300 elements can be 2100 (70 by 30) to 7,000 (70 by 100) per second. Because the detectors can be stationary and at each instant about ⅓ of them can be in use, the detector readout speed can be about 700-2400 frame per second. The flying source spot can be controlled in a stepping mode. The total exposure time for each projection can be about 0.4-1.4 millisecond.

The signal-to-noise ratio (SNR) can be used to assess the performance of the EBMCT system. While the signal is determined by the image information content and imaging physics, the noise arises from various sources in the data acquisition systems (DAS). Typically, the SNR refers to the magnitude of the signal relative to fluctuations in readings. Mathematically, it is defined as the ratio between the measured signal strength and noise deviation. The three primary factors contributing to data noise are photon noise, dark noise, and read noise, which can be readily analyzed by one skilled in the art.

The contrast resolution may be defined as the percentage of the mean difference between a region of interest and the background relative to the background. Because the EBMCT scanner emphasizes the temporal resolution, the contrast resolution is not pushed to be most sensitive. The contrast resolution can be set to 10%. To distinguish a region of interest with a 50% confidence, there can be an empirical relationship $$C = k \frac{\Delta p}{D} \frac{\sigma}{\mu_b},$$

where C denotes the contrast resolution, k a constant between 2 and 5, $\Delta p$ the pixel size, D the diameter of the target of interest, $\sigma$ noise and $\mu_b$ the background mean. Set C=10%, k=3.5, $\Delta p$=0.1 mm, D=1 mm, and obtain a signal-to-noise ration SNR $\mu_b/\sigma$=3.5.

The spatial resolution of the EBMCT system can be estimated from the focal spot blurring $\beta_f$ and detector blurring $\beta_d$, which are function of the magnification of the system and approximately given by $\beta_f$=$f$(M−1)/M and $\beta_d$=d/M, respectively, where $f$ denotes the inherent focal spot size, d the size of the detector cell, and M the magnification factor of the system defined as the ratio of the source-to-detector distance and the source-to-axis distance. The spatial resolution of the system is the square root of the sum of the squares of the individual blurring components. For example, with about 250 µm focal spot, 150 µm detector size (binning mode) and 3 fold magnification, about 180 μm spatial resolution can be obtained.

The finite area of the X-ray focal spot causes structural details to be smeared, leading to the source blurring. The spot size also varies with the applied tube voltage (U) and current (I). It was found that the size of the focus spot could be modeled as proportional to I and inversely proportional to $U^{3/2}$. In the current EBCT the beam spot size is between 0.6 mm to 1.2 mm in the azimuthal direction and between 1.1 mm to 1.4 mm in length for 130 kV and 140 kV protocols. The high voltage supply would stay within 0.1% of the nominal voltage. The spot intensity distribution can be modeled as being circular or Gaussian. Given the current technology, focal spot size would be around 0.2-0.3 mm in diameter. Actually, the focus spot may be asymmetric due to the nonstandard nature of the spiral locus and the imperfect focusing of the electron-beam. As a result, the focal spot may vary spatially.

The source blurring can be compensated for with collimated source techniques and/or digital deconvolution methods. The source collimation can be achieved with an effective target configuration, so that the X-ray spot is not spread widely. This can be implemented by sophisticated fabrication of the target in which the tungsten-based material is only limited to the desirable positions along the spiral (or non-standard spiral, saddle, etc . . . ) structure of much less efficient X-ray generating material. When a relatively large focus spot size is used for the EBMCT system, source-deblurring algorithms can reduce the source size retrospectively. When the size of a field of view is small relative to its distance from the X-ray source, the weak perspective model is quite accurate. Under the weak perspective, a divergent beam projection can be well approximated as a scaled parallel-beam projection. Consequently, the spatially variant blurring model due to the finite size of the X-ray source can be simplified as a spatially invariant blurring model. First invert such a simplified source-blurring model. Then, if needed, fully 3D iterative deblurring methods can be used, assuming a spatially variant imaging model.

For the electron-beam CT/micro-CT configuration, a variable radius spiral locus can be described as $$C := \left\{ y(s) \in R^3 : y_1 = R(s)\cos(s),\ y_2 = R(s)\sin(s),\ y_3 = \frac{sh}{2\pi} \right\},\ s \in R \quad (36)$$

Figure 2:
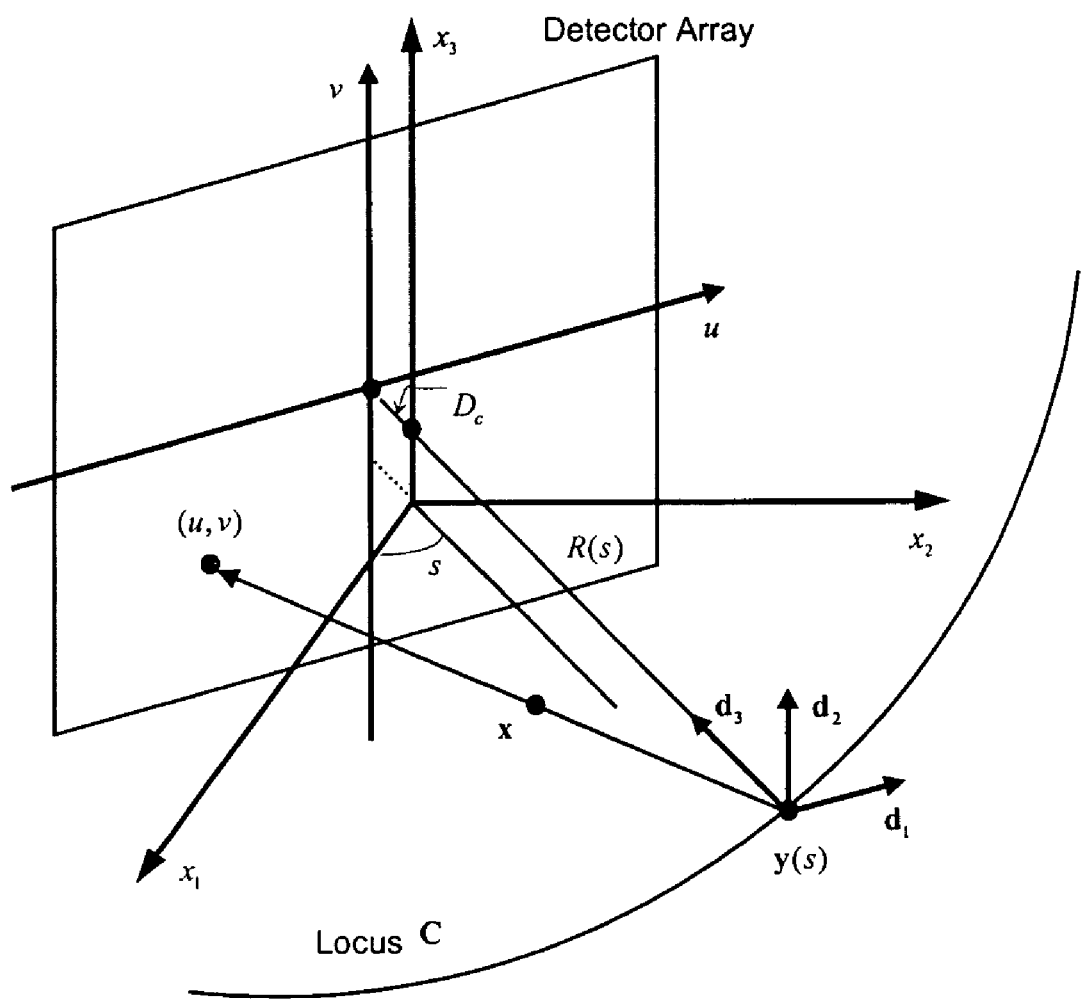
FIG. 2 shows a local coordinate system for cone-beam projection measurement on a planar detector.

For a given s, define a local coordinate system by its three orthogonal unit directional vectors: $d_1 := (-\sin(s),\ \cos(s), 0)$, $d_2 := (0,0,1)$ and $d_3 := (-\cos(s),\ -\sin(s), 0)$ Shown as in FIG. 2, cone-beam data can be measured on a planar detector array parallel to $d_1$ and $d_2$ at a distance D(s) from y(s) with $D(s) = R(s) + D_c$, where $D_c$ is a constant or variable. A detector position in the array is given by a pair of values (u, v), which are signed distances along $d_1$ and $d_2$ respectively. Let (u, v)=(0, 0) correspond to the orthogonal projection of y(s) onto the detector array. If s and D(s) are given, (u, v) are determined by β, and vice versa. For fixed y(s), D(s) is constant, and equispatial cone-beam projection data are denoted as g(s, u, v) with $$u = \frac{D(s)\beta \cdot d_1}{\beta \cdot d_3},\ v = \frac{D(s)\beta \cdot d_2}{\beta \cdot d_3} \quad (37)$$

Then, either generalized FBP or BPF algorithms can be applied for exact image reconstruction.

Parameters of the exemplary device and system are listed in Table 4.

TABLE 4

Exemplary Specifications of the Electron-Beam Micro-CT

| System Specifications | | X-Ray Source | | X-Ray Camera | |
|---|---|---|---|---|---|
| Field of View | 30-50 mm | Target Material | Tungsten-based | Camera Head | Spectral Instruments 1000 Series |
| Source to Axis Distance | 30-60 mm | | | | |
| Source to Detector Distance | 125-150 mm | Tube Voltage | 40-80 kVp | Detector Cell | 50-200 μm |
| Number of Views per Rotation | 30-100 | Tube Current | 10-100 mA | Frame Speed | 700-2,400 fps |
| Spatial & Contrast Resolution | ~100 μm, ~5% | Focus Spot | 50-200 μm | Dynamic Range | 12-16 bits |
| Scanning Speed | ~50 Hz (~70 half-scans per second) | Control Mode | Stepping, 0.4-1.4 ms | Detector Noise | 1000 electrons |

Figure 10:
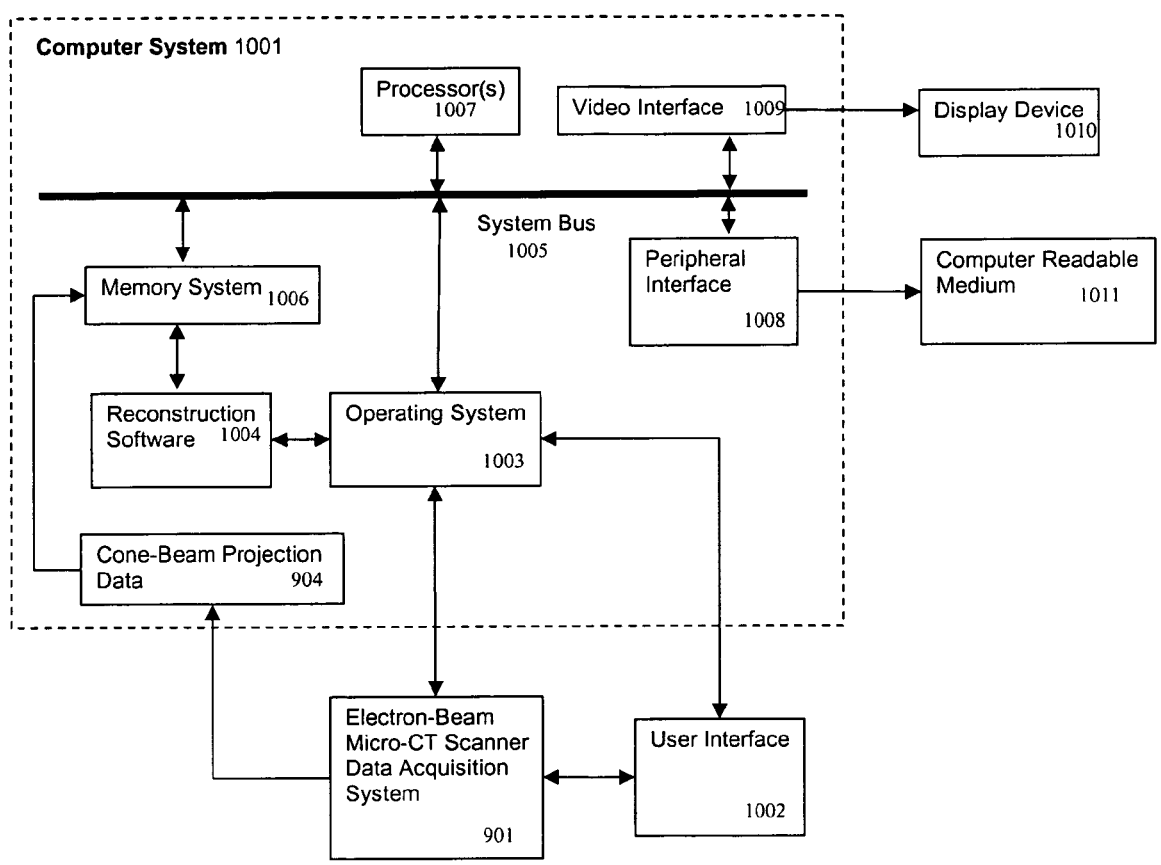
FIG. 10 shows a block diagram describing exemplary components involved in implementing the disclosed systems and methods.

By way of example, and not limitation, FIG. 10 illustrates components of an exemplary EBMCT reconstruction system. This exemplary system is only an example of an system and is not intended to suggest any limitation as to the scope of use or functionality of system architecture. Neither should the system be interpreted as having any dependency or requirement relating to any one or combination of components illustrated in the exemplary system.

The method can be operational with numerous other general purpose or special purpose computing system environments or configurations. Examples of well known computing systems, environments, and/or configurations that may be suitable for use with the system and method include, but are not limited to, personal computers, server computers, laptop devices, and multiprocessor systems. Additional examples include set top boxes, programmable consumer electronics, network PCs, minicomputers, mainframe computers, distributed computing environments that include any of the above systems or devices, and the like.

The method may be described in the general context of computer instructions, such as program modules, being executed by a computer. Generally, program modules include routines, programs, objects, components, data structures, etc. that perform particular tasks or implement particular abstract data types. The system and method may also be practiced in distributed computing environments where tasks are performed by remote processing devices that are linked through a communications network. In a distributed computing environment, program modules may be located in both local and remote computer storage media including memory storage devices.

The processing of the disclosed method can be performed by software components. The disclosed method may be described in the general context of computer-executable instructions, such as program modules, being executed by one or more computers or other devices. Generally, program modules include computer code, routines, programs, objects, components, data structures, etc. that perform particular tasks or implement particular abstract data types. The disclosed method may also be practiced in grid-based and distributed computing environments where tasks are performed by remote processing devices that are linked through a communications network. In a distributed computing environment, program modules may be located in both local and remote computer storage media including memory storage devices.

Figure 9:
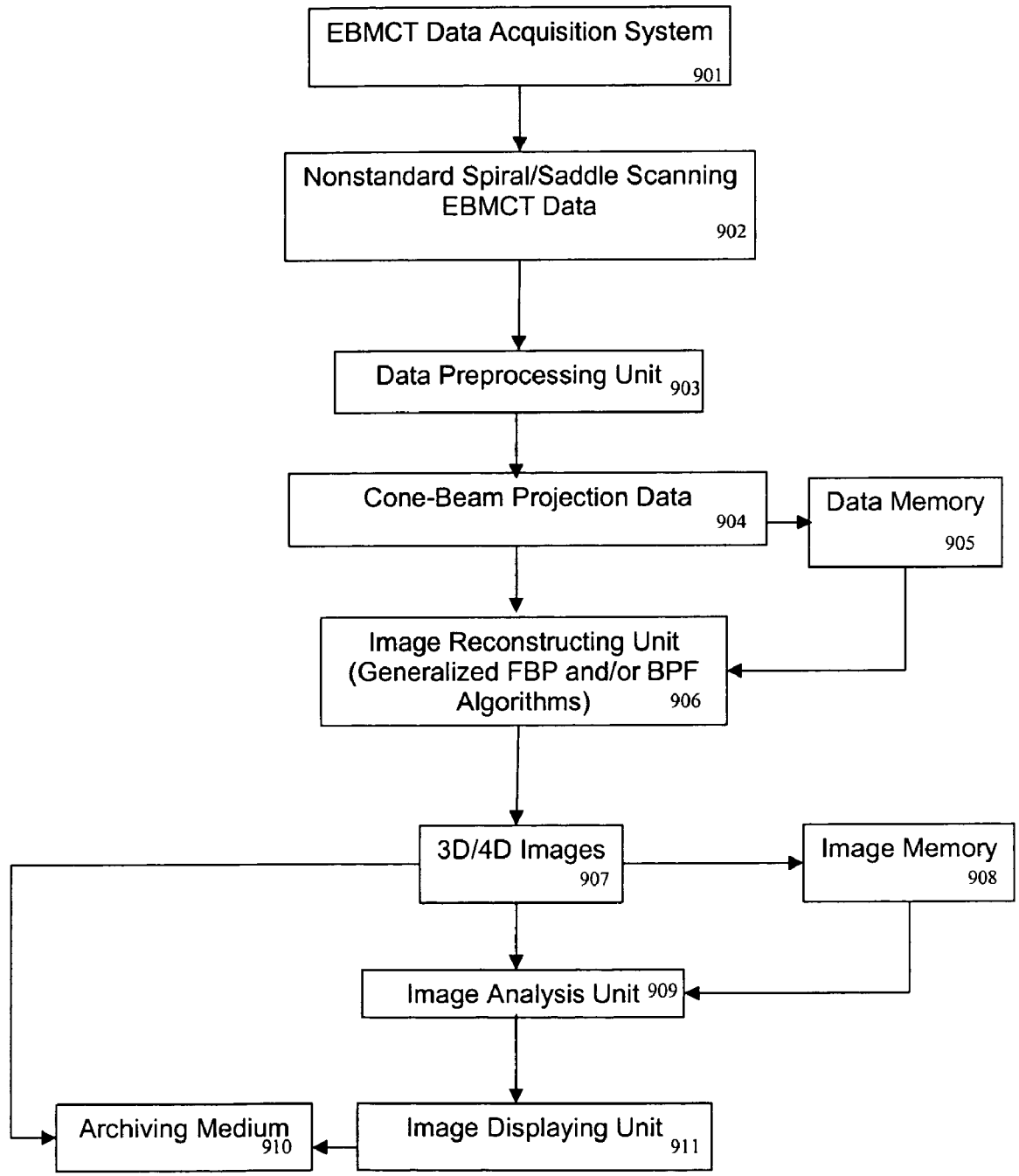
FIG. 9 shows a flowchart describing an exemplary image reconstruction process implementing the disclosed systems and methods.

Under a general or dedicated computer system 1001 support, such components may include, but are not limited to, a memory system 1006, processor(s) 1007, reconstruction software 1004, and a system bus 1005 that couples various system components. The computer-based system of FIG. 10 can be used to execute exemplary steps of the flow chart in FIG. 9. The user interface 1002, connected to the computer system 1001, can be employed to acquire EBMCT data 901. These non-standard spiral and/or saddle scanning EBMCT data 902 can then be passed through a data pre-processing unit 903. Processor(s) 1007 performs step 903 of preprocessing the data 902. Then, the cone-beam projection data 904 can be obtained and stored in data memory 905 that can be part of the memory system 1006. The image reconstructing unit 906 implementing the algorithms of the present invention can utilize reconstruction software 1004 interacting with the operating system 1003, processor(s) 1007, and memory system 1006 to create 3D/4D images 907 that can be visualized and analyzed on the display device 1010, and stored in image memory 908 that can be part of the memory system 1006. The 3D/4D images 907 can also be stored on an archiving medium 910. This medium can be part of memory system 1006 or computer readable medium 1011 by way of the peripheral interface 1008. The image analysis unit 909 can pass the final image to the image display unit 911. The image display unit can utilize the video interface 1009 to output a final image onto a display device 1010 such as a monitor.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

FBP and BPF Reconstructions with Non-Standard Spiral Loci

In this example, two variable radius loci for evaluation and verification of the proposed algorithms were used, which are described by $R(S) = R_a + R_b \cos(s)$ and $$R(s) = R_a + \frac{R_b}{2\pi} s.$$

For convenience, they are referred to as NVRL (nonlinear variable radius locus) and LVRL (linear variable radius locus), respectively. $R_a$=87.5 cm and $R_b$=12.5 cm was set for NVRL, while $R_a$=90.0 cm and $R_b$=30.0 cm was set for LVRL. In the following example, unless otherwise stated others parameters should remain the same as in Table 1.

TABLE 1

| Cone-beam imaging parameters used in the example | |
|---|---|
| Origin to detector distance ($D_c$) | 75 cm |
| Helical pitch (h) | 12.5 cm |
| Object radius (r) | 25 cm |
| Scanning range | $s \in [-2\pi, 2\pi]$ |
| Scanning angle sampling interval ($\Delta s$) | $\pi/400$ |
| Horizontal detector sampling interval ($\Delta u$) | 0.333 cm |
| Vertical detector sampling interval ($\Delta v$) | 0.333 cm |
| Reconstruction matrix | 256 × 256 × 256 |

The modified 3D Shepp-Logan phantom was used, which includes 10 ellipsoids with normalized parameters as listed in Table 2, where ($x_0$, $y_0$, $z_0$) are the coordinates of an ellipsoid center, (a, b, c) the x, y, z semi-axes, $\phi$ is the rotation angle of an ellipsoid (about z axis), and $f$ is the relative X-ray linear absorption coefficient. The effective X-ray absorption coefficient of a point is the sum of the relative parameters of those ellipsoids that contain the point.

Figure 5:
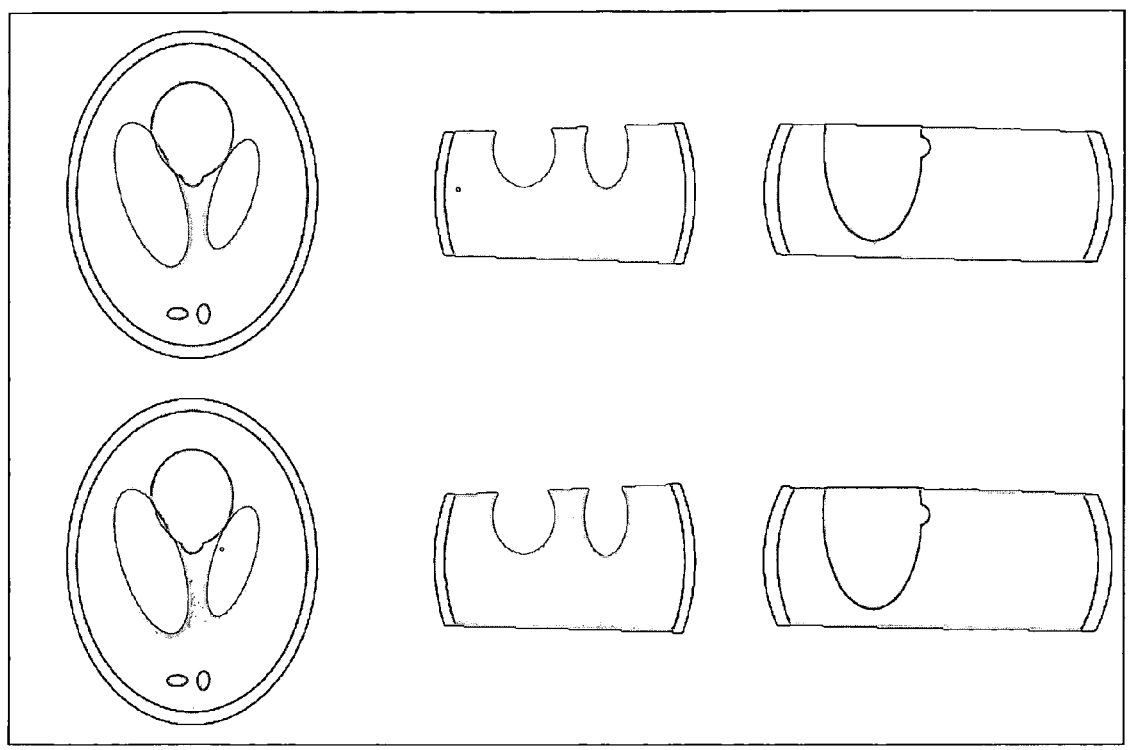
FIG. 5 shows reconstructed slices of the 3D Shepp-Logan Phantom by the FBP algorithm

Following the same numerical implementation steps as that of the FBP algorithm for standard spiral cone beam CT, the FBP algorithm described herein was implemented for variable radius spiral cone-beam CT in MatLab and C. FIG. 5 shows some reconstructed slices by the Katsevich-type FBP algorithm. The first row presents slices reconstructed from cone-beam projections collected from NVRL, while the second row is for the counterparts from LVRL. The left column includes slices at z=−6.25 cm, the middle column at y=0 cm, and right column at x=0 cm. The gray-level interval [0.1, 0.3] was mapped [0, 255] for visualization. As shown in FIG. 5, it can be seen that the FBP algorithm worked well for both NVRL and LVRL.

TABLE 2

| Normalized parameters of the modified 3D Shepp-Logan phantom | | | | | | | |
|---|---|---|---|---|---|---|---|
| No. | a | b | c | $x_0$ | $y_0$ | $z_0$ | $\phi$ | f |
| 1 | 0.6900 | 0.920 | 0.900 | 0 | 0 | 0 | 0 | 1.0 |
| 2 | 0.6624 | 0.874 | 0.880 | 0 | 0 | 0 | 0 | −0.8 |
| 3 | 0.4100 | 0.160 | 0.210 | −0.22 | 0 | −0.250 | 108 | −0.2 |
| 4 | 0.3100 | 0.110 | 0.220 | 0.22 | 0 | −0.25 | 72 | −0.2 |
| 5 | 0.2100 | 0.250 | 0.500 | 0 | 0.35 | −0.25 | 0 | 0.2 |
| 6 | 0.0460 | 0.046 | 0.046 | 0 | 0.1 | −0.25 | 0 | 0.2 |
| 7 | 0.0460 | 0.023 | 0.020 | −0.08 | −0.65 | −0.25 | 0 | 0.1 |
| 8 | 0.0460 | 0.023 | 0.020 | 0.06 | −0.65 | −0.25 | 90 | 0.1 |
| 9 | 0.0560 | 0.040 | 0.100 | 0.06 | −0.105 | 0.625 | 90 | 0.2 |
| 10 | 0.0560 | 0.056 | 0.100 | 0 | 0.100 | 0.625 | 0 | −0.2 |

Figure 6:
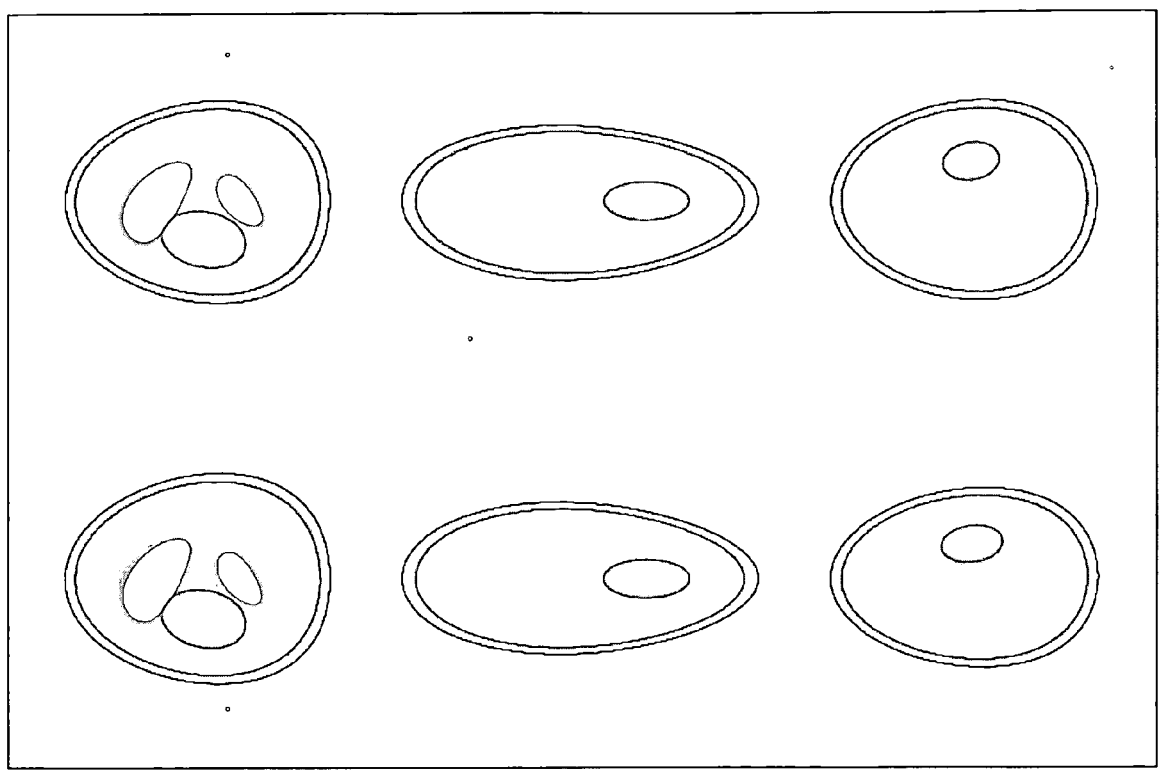
FIG. 6 shows reconstructed slices of the 3D Shepp-Logan Phantom by the BPF algorithm FIGS. 7(a,b,c, & d) shows BPF reconstructions with a non-standard saddle locus. (a) & (b) Reconstructions from two complementary PI-arcs for $S_b=0.6\pi$ and $S_f \in [1.5\pi, 1.7\pi]$, (c) & (d) from two complementary PI-arcs for $S_b=-0.8\pi$ and $S_f \in [0.1\pi, 0.3\pi]$. The display window is [0,0.4].

Also, the BPF algorithm was implemented for variable radius spiral cone-beam CT in MatLab. The modified 3D Shepp-Logan phantom on PI-lines specified by a fixed $s_b$ and a set of $s_t$. FIG. 6 shows representative reconstruction results. The first row gives slices reconstructed from cone-beam projections collected from NVRL, while the second row is for LVRL. The PI-lines for the left column are $s_b=-\pi$ and $s_t \in [-0.32\pi, 0.32\pi]$, the PI-lines for the middle column $s_b=-0.5\pi$ and $s_t \in [0.18\pi, 0.82\pi]$, and the PI-lines for the right column $s_b=0$ and $s_t \in [0.68\pi, 1.32\pi]$. The gray-level range was windowed as described above. These slices appear somewhat "distorted" because they are not displayed in the Cartesian coordinate system, but for any given point x, the reconstruction value can be readily obtained with 3D interpolation.

BPF Reconstruction with a Non-standard Saddle Curve

Figure 7:
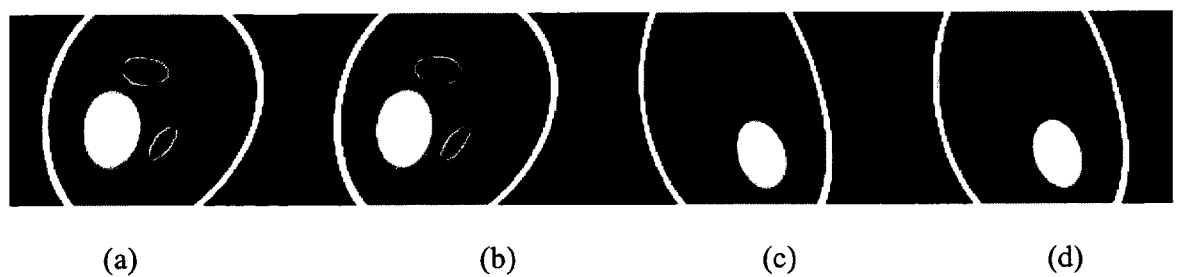

To verify the correctness of the generalized BPF algorithm, a non-standard saddle locus was selected based on J D Pack, et al., *Proc. of the VIIth Int'l Conf. on Fully 3D Reconstruction In Rad. and Nuc. Med.*, (2003) which is described by:

$R(t)=87.5+12.5\cos(t)$, and $h(t)=1.875\cos(2t)$, where the measurement unit is cm. FIG. 7 includes representative reconstruction results of the Shepp-Logan phantom. Since the locus is closed, one PI-line corresponds to two different PI-arcs whose union yields a full-scan range, which is $2\pi$. As shown in FIG. 7, reconstructions from complementary PI-arcs produced consistent results. These slices appear "distorted" because they are not displayed in the Cartesian coordinate system, but the reconstruction at any point x can be readily obtained via 3D interpolation.

While this invention has been described in connection with preferred embodiments and specific examples, it is not intended that the scope of the invention be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

REFERENCES

Barger A V, Block W. F, Toropov Y, Grist T M, and Mistretta C A, Time-resolved contrast-enhanced imaging with isotropic resolution and broad coverage using an undersampled 3D projection trajectory, Magn. Reson. Med. 48, 297-305, 2002.

Danielsson P E, Edholm P, and Seger M, Toward exact 3d-reconstruction for helical cone-beam scanning of long objects. A new detector arrangement and a new completeness condition. In: Proceedings of the 1997 International Meeting on Fully Thre-Dimensional Image Reconstruction in Radiology and Nuclear Medicine (Pittsburgh), 141-144, 1997.

Kak A. C., Slaney M., "Principles of Computerized Tomographic Imaging", SIAM, 2001.

Noo F., Pack J., and Heuscher D., "Exact helical reconstruction using native cone-beam geometries", Physics in Medicine and Biology, 48:3787-3818, 2003.

Orlov S S, Theory of three dimensional reconstruction, I Conditions for a complete set of projections, Sov. Phys. Crystallogr. Vol. 20, 312-314. II The recovery operator, ibid, Vol. 20, 429-433, 1975.

Pack J D, Noo F, and Kudo H, Investigation of a saddle trajectory for cardiac CT imaging in cone beam geometry, Proceedings of the VIIth International Conference on Fully 3D Reconstruction In Radiology and Nuclear Medicine, Saint Malo, France (Jun. 29-Jul. 4, 2003).

Pack J D, Noo F, Clackdoyle R: Cone-beam reconstruction using the backprojection of locally filtered projections. IEEE Medical Imaging 24:70-85, 2005)

Tam K C, Samarasekera S, and F Sauer (1998), Exact cone-beam CT with a spiral scan, Phys. Med. Biol. 43, 1015-1024.

Wang G, et al., "A general cone-beam reconstruction algorithm", IEEE Trans. Med. Imaging, 12, 486-496, 1993.

Wang G, Liu Y, Ye Y, Zhao S, Hsieh J, Ge S: Top-level design and preliminary physical analysis for the first electron-beam micro-CT scanner. Journal of X-Ray Sci. and Tech. 12:251-260, 2004.

Ye Y, Zhao S, Yu H and Wang G, Exact reconstruction for cone-beam scanning along nonstandard spirals and other curves Proc. SPIE 5535 293-300, 2004a.

Ye Y., Zhu J, and Wang G, Minimum Detection Windows, PI-line Existence and Uniqueness for Helical Cone-Beam Scanning of Variable Pitch, Med. Phys. 31(3), 566-572, 2004b.

Ye Y., et al., "Geometric Studies on Variable Radius Spiral Cone-Beam Scanning", Med. Phys. 31, 1473-1480, 2004c.

Ye Y, Zhao S, Yu H, Wang G: A general exact reconstruction for cone-beam CT via backprojection-filtration. To appear in IEEE Transactions on Medical Imaging, 2005.

Ye Y, Wang G: A filtered backprojection formula for exact image reconstruction from cone-beam data along a general scanning curve. Med. Phys. 32:42-48, 2005

Yu H Y, Ye Y B, Wang G: Katsevich-type algorithms for variable radius spiral cone-beam CT. Proceedings of SPIE Conference on Computed Tomography (Vol. 5535), p 550-557, August 2004

Yu H Y, Ye Y B, Zhao S Y, Wang G: A backprojected filtration algorithm for nonstandard spiral cone-beam CT with an N-PI window. Phys. Med. Biol. 50:2099-2111, 2005.

Yu H, Zhao S, Ye Y, Wang G: Exact BPF and FBP algorithms for nonstandard saddle curves. Revision submitted to Med. Phys., 2005.

Zhao S., Yu H. and Wang G., "A family of analytic algorithms for cone-beam CT," Proceedings of SPIE, Developments in X-Ray Tomography IV, vol. 5535, 318-328, SPIE Press, August, 2004.

Zhuang T, Leng S, Net B E, Chen G H: Fan-beam and cone-beam image reconstruction via filtering the backprojection image of differentiated projection data. Physics in Medicine and Biology 49:5489-5503, 2004.

Zhao S Y, Yu H Y, Wang G: A family of analytic algorithms for cone-beam CT. Proceedings of SPIE Conference on Computed Tomography (Vol. 5535), p 318-328, August 2004.

Zhao S, Yu H, Wang G: A unified framework for exact cone-beam image reconstruction formulas. Med. Phys. 32:1712-1721, 2005.

Zhu J H, Zhao S Y, Yu H Y, Lee S W, Ye Y B, Wang G: Numerical studies on Feldkamp-type and Katsevich-type algorithms for cone-beam scanning along nonstandard spirals. Proceedings of SPIE Conference on Computed Tomography (Vol. 5535), p 558-565, August 2004.

Zou Y, Pan X: An extended data function and its generalized backprojection for image reconstruction in helical cone-beam CT. Phys. Med. Biol. 49:N383-N387, 2004

Zou Y. and Pan X., "Exact image reconstruction on PI-lines in helical cone beam CT," Physics in Medicine and Biology. 49: 941-959, 2004.

What is claimed is:

1. A method of reconstructing an image from projection data provided by a tomography scanner that is based on geometric optics comprising:
   scanning an object in a cone-beam imaging geometry following a general piecewise smooth scanning path wherein projection data is generated; and
   reconstructing an image according to a closed-form formula, wherein reconstructing comprises
   calculating derivatives of projection data with respect to a source position,
   determining at least one chord that passes through a point to be reconstructed,
   performing weighted backprojection of derivatives of the projection data onto the at least one chord, generating backprojected data, and
   performing an Inverse Hilbert Transform on the back-projected data along the at least one chord, generating transformed data.

2. The method of claim 1, wherein the general piecewise smooth scanning path is a nonstandard spiral.

3. The method of claim 1, wherein the general piecewise smooth scanning path is a nonstandard saddle.

4. The method of claim 1, wherein determining a chord comprises:
   declaring a parameter $s_b$ for a first end of a corresponding interval $I_{PI}(x)$;
   declaring a parameter $s_t$ for a second end of the corresponding interval $I_{PI}(x)$;
   parameterizing a family of chords by $s_b$;
   finding a chord through a fixed point $y(s_b)$ that intersects a line V through a point x; and
   identifying $s_b$ and $s_t$ such that $s_b=s_b(x)$ and $s_t=s_t(x)$, wherein $s_b(x)$ and $s_t(x)$ are endpoints on $I_{PI}(x)$, $y(s)$ is the scanning path, and $y(s_b)$ and $y(s_t)$ are points on the scanning path that correspond to $s_b(x)$ and $s_t(x)$ that define the chord through x.

5. The method of claim 1, wherein the steps of performing weighted backprojection of derivatives of the projection data onto the at least one chord, generating backprojected data, and performing an Inverse Hilbert Transform on the back-projected data along the at least one chord, generating transformed data comprises:
   filtering the derivative data along a filtering direction, generating filtered derivative data, wherein the filtering direction is determined by a projection line from a projection point on the scanning path $y(s)$ to an image point x and by a vector $e(s, x)$ perpendicular to the projection line; and
   performing weighted backprojection of the filtered derivative data, generating an image.

6. The method of claim 5, wherein filtering the derivative data along a filtering direction, generating filtered derivative data further comprises one or more filtering paths satisfying the condition that, for vectors v whose normal plane passing through the point x intersecting the scanning path $y(s)$ at points $y(s_1), \ldots, y(s_r)$, $$\sum_{j=0}^{r} sgn[v \cdot y'(s_j)] sgn[v \cdot e(s_j, x)] = 1,$$

wherein $y'(s_j)$ is the tangential direction of the scanning path at the point $y(s_j)$.

7. The method of claim 5, wherein performing weighted backprojection comprises:
   calculating $$p(x') = \int_{s_t(x)}^{s_b(x)} \frac{G(s, \tilde{u}, \tilde{v})}{|x' - y(s)|} ds$$

with $$\tilde{u} = \frac{D(s)(x' - y(s)) \cdot d_1}{(x' - y(s)) \cdot d_3}, \tilde{v} = \frac{D(s)(x' - y(s)) \cdot d_2}{(x' - y(s)) \cdot d_3},$$

wherein p(x') is the weighted backprojection,
$G(s, \tilde{u}, \tilde{v})$ is the filtered data
$|x'-y(s)|$ is the distance between the point x' and the point parameterized by s on the scanning path $y(s)$,
$d_1$, $d_2$, and $d_3$ are local coordinate vectors in space such that $d_1$ and $d_2$ are parallel to a detector plane with $d_1$ pointing horizontally, $d_2$ pointing vertically, and $d_3$ pointing toward the detector plane,
$D(s)$ is the distance between an x-ray source $y(s)$ and the detector plane,
$\tilde{u}$ and $\tilde{v}$ are the $d_1$- and $d_2$-coordinates of n x-ray projection of x' on the detector plane from $y(s)$.

8. The method of claim 1, wherein performing an Inverse Hilbert Transform comprises:
   pre-weighting the backprojected data to attain pre-weighted data;
   applying a Hilbert transform to the pre-weighted data to attain transformed data;
   level-shifting the transformed data to attain level-shifted data; and
   post-weighting the level-shifted data.

9. The method of claim 1, further comprising:
   rebinning the transformed data into a Cartesian grid.

10. The method of claim 1, wherein performing weighted backprojection comprises:
    calculating $$p(x') = \int_{s_t(x)}^{s_b(x)} \frac{G(s, \tilde{u}, \tilde{v})}{|x' - y(s)|} ds$$

with $$\tilde{u} = \frac{D(s)(x' - y(s)) \cdot d_1}{(x' - y(s)) \cdot d_3}, \tilde{v} = \frac{D(s)(x' - y(s)) \cdot d_2}{(x' - y(s)) \cdot d_3},$$

wherein p(x') is the weighted backprojection,

G(s, ũ, ṽ) is the derivative data,

|x'−y(s)| is the distance between the point x' and the point parameterized by s on the scanning path y(s), $d_1$, $d_2$, and $d_3$ are local coordinate vectors in space such that $d_1$ and $d_2$ are parallel to a detector plane with $d_1$ pointing horizontally, $d_2$ pointing vertically, and $d_3$ pointing toward the detector plane, D(s) is the distance between an x-ray source y(s) and the detector plane, ũ and ṽ are the $d_1$- and $d_2$-coordinates of n x-ray projection of x' on the detector plane from y(s).

11. A system of reconstructing an image from projection data provided by a tomography scanner that is based on geometric optics comprising:
   a tomography scanner for scanning an object in a cone-beam imaging geometry following a general piecewise smooth scanning path, wherein projection data is generated;
   a processor programmed for performing the step of:
   reconstructing an image according to a closed-form noniterative formula that is exact, wherein reconstructing comprises
   calculating derivatives of projection data with respect to a source position,
   determining at least one chord that passes through a point to be reconstructed,
   performing weighted backprojection of derivatives of the projection data onto the at least one chord, generating backprojected data, and
   performing an Inverse Hilbert Transform on the backprojected data along the at least one chord, generating transformed data.

12. The system of claim 11, wherein the tomography scanner has a detector readout speed from about 700 to about 1,400 frames per second.

13. The system of claim 11, wherein the tomography scanner has at least one detector arranged in a 2D matrix.

14. The system of claim 13, wherein the detector cells are arranged in a 2D matrix, such as from about 100 by 100 to about 1000 by 1000.

15. The system of claim 11, wherein the general piecewise smooth scanning path is a nonstandard spiral.

16. The system of claim 11, wherein the general piecewise smooth scanning path is a nonstandard saddle.

17. The system of claim 11, wherein the scanner has a scanning speed from about 25 to about 50 Hz.

18. The system of claim 11, wherein determining a chord comprises:
   declaring a parameter $s_b$ for a first end of a corresponding interval $I_{PI}(x)$;
   declaring a parameter $s_t$ for a second end of the corresponding interval $I_{PI}(x)$;
   parameterizing a family of chords by $s_b$;
   finding a chord through a fixed point $y(s_b)$ that intersects a line V through a point x and; and
   identifying $s_b$ and $s_t$ such that $s_b = s_b(x)$ and $s_t = s_t(x)$, wherein $s_b(x)$ and $s_t(x)$ are endpoints on $I_{PI}(x)$, y(s) is the scanning path, and $y(s_b)$ and $y(s_t)$ are points on the scanning path that correspond to $s_b(x)$ and $s_t(x)$ that define the chord through x.

19. The system of claim 11, wherein the steps of performing weighted backprojection of derivatives of the projection data onto the at least one chord, generating backprojected data, and performing an Inverse Hilbert Transform on the backprojected data along the at least one chord, generating transformed data comprise:

filtering the derivative data along a filtering direction, generating filtered derivative data, wherein the filtering direction is determined by a projection line from a projection point on the scanning path y(s) to an image point x and by a vector e(s, x) perpendicular to the projection line; and performing weighted backprojection of the filtered derivative data, generating an image.

20. The system of claim 19, wherein filtering the derivative data along a filtering direction, generating filtered derivative data further comprises one or more filtering paths satisfying the condition that, for vectors v whose normal plane passing through the point x intersecting the scanning path y(s) at points $y(s_1), \ldots, y(s_r)$, $$\sum_{j=0}^{r} sgn[v \cdot y'(s_j)] sgn[v \cdot e(s_j, x)] = 1,$$

wherein $y'(s_j)$ is the tangential direction of the scanning path at the point $y(s_j)$.

21. The system of claim 19, wherein performing weighted backprojection comprises:
   calculating $$p(x') = \int_{s_t(x)}^{s_b(x)} \frac{G(s, \tilde{u}, \tilde{v})}{|x' - y(s)|} ds$$

with $$\tilde{u} = \frac{D(s)(x' - y(s)) \cdot d_1}{(x' - y(s)) \cdot d_3}, \tilde{v} = \frac{D(s)(x' - y(s)) \cdot d_2}{(x' - y(s)) \cdot d_3},$$

wherein p(x') is the weighted backprojection,

G(s, ũ, ṽ) is the filtered data,

|x'−y(s)| is the distance between the point x' and the point parameterized by s on the scanning path y(s), $d_1$, $d_2$, and $d_3$ are local coordinate vectors in space such that $d_1$ and $d_2$ are parallel to a detector plane with $d_1$ pointing horizontally, $d_2$ pointing vertically, and $d_3$ pointing toward the detector plane, D(s) is the distance between an x-ray source y(s) and the detector plane, ũ and ṽ are the $d_1$- and $d_2$-coordinates of n x-ray projection of x' on the detector plane from y(s).

22. The system of claim 11, wherein performing an Inverse Hilbert Transform comprises:
   pre-weighting the backprojected data to attain pre-weighted data;
   applying a Hilbert transform to the pre-weighted data to attain transformed data;
   level-shifting the transformed data to attain level-shifted data; and
   post-weighting the level-shifted data.

23. The system of claim 11, further comprising:
   rebinning the transformed data into a Cartesian grid.

24. The system of claim 11, wherein performing weighted backprojection comprises:
calculating with $$p(x') = \int_{s_t(x)}^{s_b(x)} \frac{G(s, \tilde{u}, \tilde{v})}{|x' - y(s)|} ds$$

with $$\tilde{u} = \frac{D(s)(x' - y(s)) \cdot d_1}{(x' - y(s)) \cdot d_3}, \tilde{v} = \frac{D(s)(x' - y(s)) \cdot d_2}{(x' - y(s)) \cdot d_3},$$

wherein p(x') is the weighted backprojection,
G(s, ũ, ṽ) is the derivative data,
|x'−y(s)| is the distance between the point x' and the point parameterized by s on the scanning path y(s),
$d_1$, $d_2$, and $d_3$ are local coordinate vectors in space such that $d_1$ and $d_2$ are parallel to a detector plane with $d_1$ pointing horizontally, $d_2$ pointing vertically, and $d_3$ pointing toward the detector plane,
D(s) is the distance between an x-ray source y(s) and the detector plane,
ũ and ṽ are the $d_1$- and $d_2$-coordinates of n x-ray projection of x' on the detector plane from y(s).

25. A computer readable medium having computer executable instructions for reconstructing an image from projection data provided by a tomography scanner that is based on geometric optics comprising:
reconstructing an image according to a closed-form formula that is exact from projection data wherein the data is acquired as the result of a scan following a general piecewise smooth scanning path, wherein reconstructing comprises
calculating derivatives of projection data with respect to a source position,
determining at least one chord that passes through a point to be reconstructed,
performing weighted backprojection of derivatives of the projection data onto the at least one chord, generating backprojected data, and
performing an Inverse Hubert Transform on the backprojected data along the at least one chord, generating transformed data.

26. The computer readable medium of claim 25, wherein the general piecewise smooth scanning path is a nonstandard spiral.

27. The computer readable medium of claim 25, wherein the general piecewise smooth scanning path is a nonstandard saddle.

28. The computer readable medium of claim 25, wherein determining a chord comprises:
declaring a parameter $s_b$ for a first end of a corresponding interval $I_{PI}(x)$;
declaring a parameter $s_t$ for a second end of the corresponding interval $I_{PI}(x)$;
parameterizing a family of chords by $s_b$;
finding a chord through a fixed point $y(s_b)$ that intersects a line V through a point x; and
identifying $s_b$ and $s_t$ such that $s_b = s_b(x)$ and $s_t = s_t(x)$, wherein $s_b(x)$ and $s_t(x)$ are endpoints on $I_{PI}(x)$, y(s) is the scanning path, and $y(s_b)$ and $y(s_t)$ are points on the scanning path that correspond to $s_b(x)$ and $s_t(x)$ that define the chord through x.

29. The computer readable medium of claim 25, wherein the steps of performing weighted backprojection of derivatives of the projection data onto the at least one chord, generating backprojected data, and performing an Inverse Hilbert Transform on the backprojected data along the at least one chord, generating transformed data comprise:
filtering the derivative data along a filtering direction, generating filtered derivative data, wherein the filtering direction is determined by a projection line from a projection point on the scanning path y(s) to an image point x and by a vector e(s, x) perpendicular to the projection line; and
performing weighted backprojection of the filtered derivative data, generating an image.

30. The computer readable medium of claim 29, derivative the derivative data along a filtering direction, generating filtered data further comprises one or more filtering paths satisfying the condition that, for vectors v whose normal plane passing through the point x intersecting the scanning path y(s) at points $y(s_1), \ldots, y(s_r)$, $$\sum_{j=0}^{r} sgn[v \cdot y'(s_j)] sgn[v \cdot e(s_j, x)] = 1,$$

wherein $y'(s_j)$ is the tangential direction of the scanning path at the point $y(s_j)$.

31. The computer readable medium of claim 29, wherein performing weighted backprojection comprises:
calculating $$p(x') = \int_{s_t(x)}^{s_b(x)} \frac{G(s, \tilde{u}, \tilde{v})}{|x' - y(s)|} ds$$

with $$\tilde{u} = \frac{D(s)(x' - y(s)) \cdot d_1}{(x' - y(s)) \cdot d_3}, \tilde{v} = \frac{D(s)(x' - y(s)) \cdot d_2}{(x' - y(s)) \cdot d_3},$$

wherein p(x') is the weighted backprojection,
G(s, ũ, ṽ) is the filtered data,
|x'−y(s)| is the distance between the point x' and the point parameterized by s on the scanning path y(s),
$d_1$, $d_2$, and $d_3$ are local coordinate vectors in space such that $d_1$ and $d_2$ are parallel to a detector plane with $d_1$ pointing horizontally, $d_2$ pointing vertically, and $d_3$ pointing toward the detector plane,
D(s) is the distance between an x-ray source y(s) and the detector plane,
ũ and ṽ are the $d_1$- and $d_2$-coordinates of n x-ray projection of x' on the detector plane from y(s).

32. The computer readable medium of claim 25, wherein performing an Inverse Hilbert Transform comprises:
pre-weighting the backprojected data to attain pre-weighted data;
applying a Hilbert transform to the pre-weighted data to attain transformed data;
level-shifting the transformed data to attain level-shifted data; and
post-weighting the level-shifted data.

33. The computer readable medium of claim 25, further comprising:

rebinning the transformed data into a Cartesian grid.

34. The computer readable medium of claim 25, wherein performing weighted backprojection comprises:

calculating $$p(x') = \int_{s_t(x)}^{s_b(x)} \frac{G(s, \tilde{u}, \tilde{v})}{|x' - y(s)|} ds$$

with $$\tilde{u} = \frac{D(s)(x' - y(s)) \cdot d_1}{(x' - y(s)) \cdot d_3}, \quad \tilde{v} = \frac{D(s)(x' - y(s)) \cdot d_2}{(x' - y(s)) \cdot d_3},$$

wherein p(x') is the weighted backprojection,

G(s, ũ, ṽ) is the derivative data,

|x'−y(s)| is the distance between the point x' and the point parameterized by s on the scanning path y(s), $d_1$, $d_2$, and $d_3$ are local coordinate vectors in space such that $d_1$ and $d_2$ are parallel to a detector plane with $d_1$ pointing horizontally, $d_2$ pointing vertically, and $d_3$ pointing toward the detector plane, D(s) is the distance between an x-ray source y(s) and the detector plane, ũ and ṽ are the $d_1$- and $d_2$-coordinates of n x-ray projection of x' on the detector plane from y(s).

* * * * *